(12) United States Patent
Bagby

(10) Patent No.: US 7,553,313 B2
(45) Date of Patent: Jun. 30, 2009

(54) APPARATUS AND METHOD FOR PREPARING A SPINAL IMPLANT SURGICAL SITE FOR RECEIVING A SPINAL FUSION IMPLANT

(75) Inventor: George W. Bagby, Spokane, WA (US)

(73) Assignee: The G.W. Bagby II Family Limited Liability Corporation, Spokane, WA (US)

(*) Notice: Subject to any disclaimer, the term of this patent is extended or adjusted under 35 U.S.C. 154(b) by 486 days.

(21) Appl. No.: 11/224,412

(22) Filed: Sep. 10, 2005

(65) Prior Publication Data

US 2006/0004370 A1 Jan. 5, 2006

Related U.S. Application Data

(63) Continuation of application No. 10/775,837, filed on Feb. 9, 2004, now abandoned, which is a continuation of application No. 10/039,384, filed on Dec. 31, 2001, now Pat. No. 6,689,167.

(51) Int. Cl.
  *A61F 5/00* (2006.01)
  *A61D 1/04* (2006.01)
  *A61F 2/44* (2006.01)
(52) U.S. Cl. .............. 606/86 A; 623/17.16; 606/279
(58) Field of Classification Search ... 623/17.11–17.16; 606/53–79, 86 A, 279
  See application file for complete search history.

(56) References Cited

U.S. PATENT DOCUMENTS

| 4,501,269 A | 2/1985 | Bagby | 128/92 G |
| 4,662,891 A | 5/1987 | Noiles | 623/22 |
| 4,778,469 A | 10/1988 | Lin et al. | 623/16 |
| 4,828,563 A | 5/1989 | Muller-Lierheim | 623/16 |
| 4,834,757 A | 5/1989 | Brantigan | 623/17 |
| 4,878,915 A * | 11/1989 | Brantigan | 623/17.11 |
| 4,898,161 A | 2/1990 | Grundei | 606/105 |
| 4,946,378 A | 8/1990 | Hirayama et al. | 623/17 |
| 4,961,740 A | 10/1990 | Ray et al. | 606/61 |

(Continued)

FOREIGN PATENT DOCUMENTS

DE 3505567 A1 6/1986

(Continued)

OTHER PUBLICATIONS

"Stress Shielding Reduced by a Silicon Plate-Bone Interface", 60(5):611-6, *Acta Orthop Scand*, pp. 611-616; 1989; Donna L. Korvick, Jarrett W. Newbrey, George W. Bagby, Ghery D. Pettit & James D. Lincoln.

(Continued)

*Primary Examiner*—Suzette J Gherbi
(74) *Attorney, Agent, or Firm*—Wells St. John P.S.

(57) ABSTRACT

An apparatus is provided for preparing a spinal implant surgical site for receiving a spinal fusion implant. The apparatus includes a drive shaft, a handle, and a hollow, cylindrical cutting body. The handle is carried by the drive shaft, the hollow, cylindrical cutting body is provided at a leading end of the drive shaft. The cylindrical cutting body has an open leading end, a plurality of circumferentially spaced-apart cutting teeth provided on the open leading end, and a plurality of circumferentially spaced-apart gullets each provided between an adjacent pair of the cutting teeth. A method is also provided.

24 Claims, 19 Drawing Sheets

U.S. PATENT DOCUMENTS

| | | | |
|---|---|---|---|
| 5,015,247 A | 5/1991 | Michelson | 606/61 |
| 5,055,104 A | 10/1991 | Ray | 606/61 |
| 5,074,880 A | 12/1991 | Mansat | 623/20 |
| 5,084,050 A | 1/1992 | Draenert | 606/77 |
| 5,171,327 A | 12/1992 | Koch et al. | 623/16 |
| 5,263,953 A | 11/1993 | Bagby | 606/61 |
| 5,403,136 A | 4/1995 | Mathys | 411/310 |
| 5,423,817 A | 6/1995 | Lin | 606/61 |
| 5,443,515 A | 8/1995 | Cohen et al. | 623/17 |
| 5,489,307 A | 2/1996 | Kuslich et al. | 623/17 |
| 5,489,308 A | 2/1996 | Kuslich et al. | 623/17 |
| 5,534,029 A | 7/1996 | Shima | 623/17 |
| 5,534,031 A | 7/1996 | Matsuzaki et al. | 623/17 |
| 5,571,192 A | 11/1996 | Schonhoffer | |
| 5,591,235 A | 1/1997 | Kuslich | 623/17 |
| 5,645,598 A | 7/1997 | Brosnahan, III | 623/17 |
| 5,665,122 A | 9/1997 | Kambin | 623/17 |
| 5,702,455 A | 12/1997 | Saggar | 623/17 |
| 5,709,683 A | 1/1998 | Bagby | 606/61 |
| 5,720,748 A | 2/1998 | Kuslich et al. | 606/80 |
| 5,800,550 A * | 9/1998 | Sertich | 623/17.16 |
| 5,904,719 A | 5/1999 | Errico et al. | 623/17 |
| 5,906,616 A | 5/1999 | Pavlov et al. | 606/61 |
| 5,968,098 A | 10/1999 | Winslow | 623/17 |
| 6,010,502 A | 1/2000 | Bagby | 606/61 |
| 6,015,436 A | 1/2000 | Schonhoffer | 623/17 |
| 6,039,762 A | 3/2000 | McKay | |
| 6,080,155 A * | 6/2000 | Michelson | 606/86 A |
| 6,346,122 B1 | 2/2002 | Picha et al. | |
| 6,371,986 B1 | 4/2002 | Bagby | |
| 6,413,278 B1 | 7/2002 | Marchosky | |
| 6,436,098 B1 | 8/2002 | Michelson | |
| 6,447,545 B1 | 9/2002 | Bagby | |
| 6,605,089 B1 | 8/2003 | Michelson | |
| 6,689,167 B2 | 2/2004 | Bagby | |

FOREIGN PATENT DOCUMENTS

| | | |
|---|---|---|
| EP | 0307241 | 9/1988 |

OTHER PUBLICATIONS

"Transmission of Disease Through Transplantation of Musculoskeletal Allografts", 77-A, pp. 1742-1754; Nov. 1995; *The Journal of Bone and Joint Surgery*.

"Anterior Cervical Interbody Fusion with Threaded Cylindrical Bone", J. Neurosurg., vol. 63; pp. 750-753; Nov. 1985; Jose M. Otero Vich, M. D.

* cited by examiner

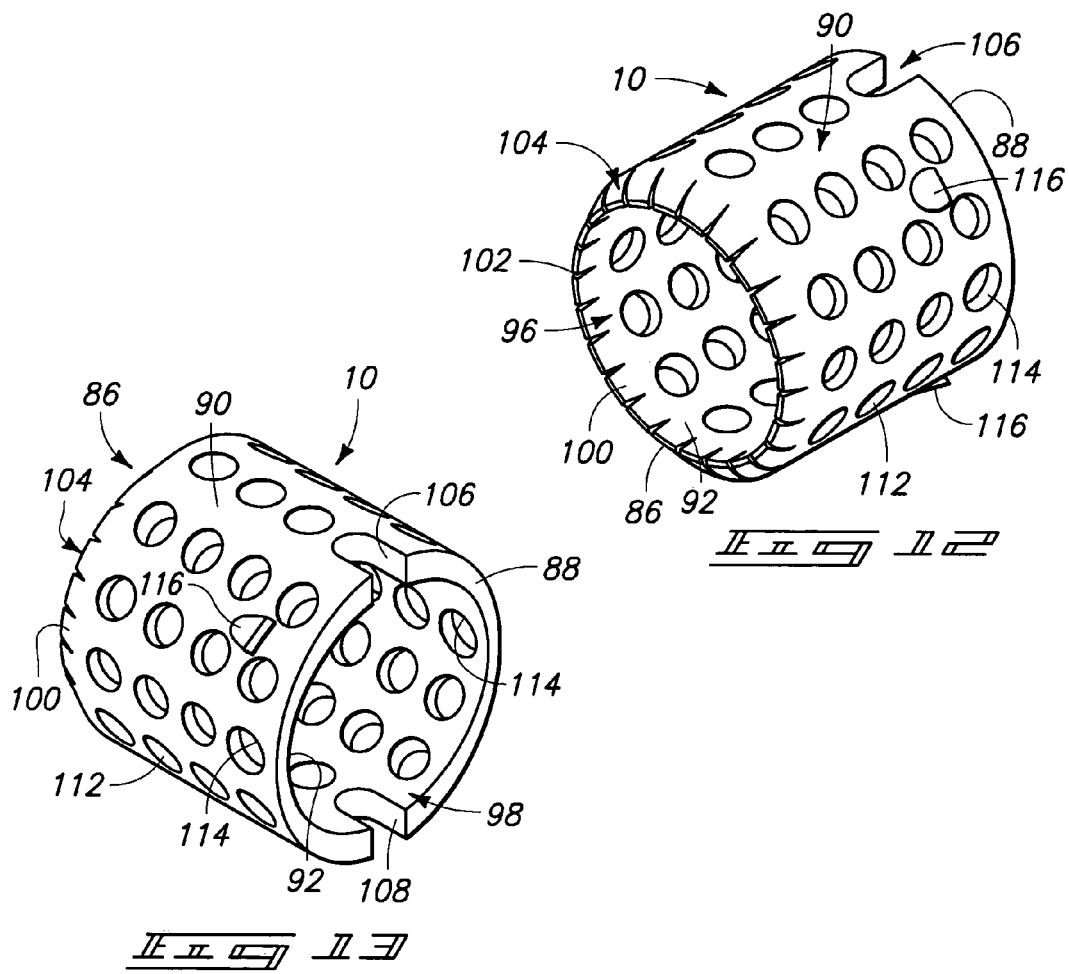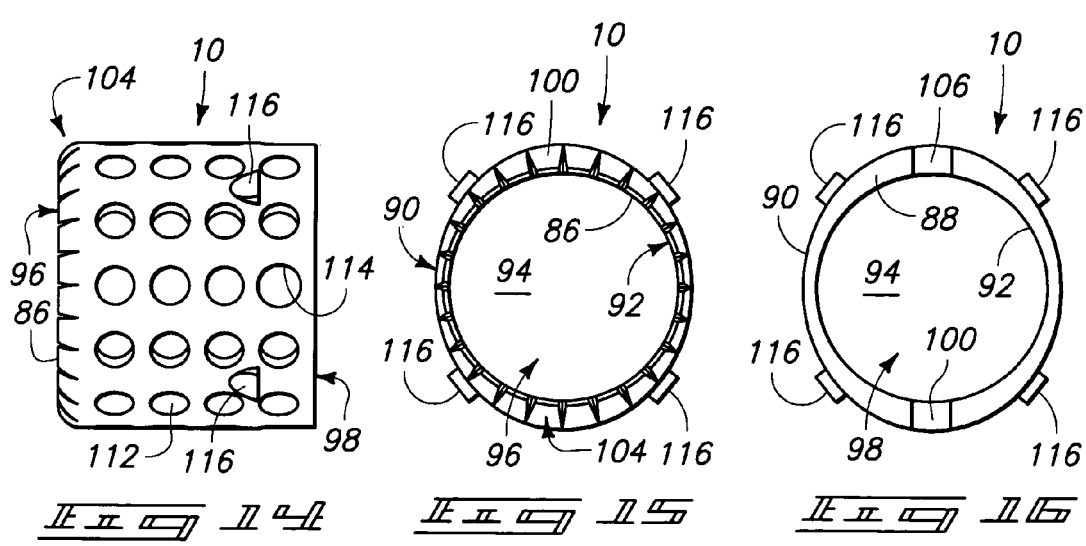

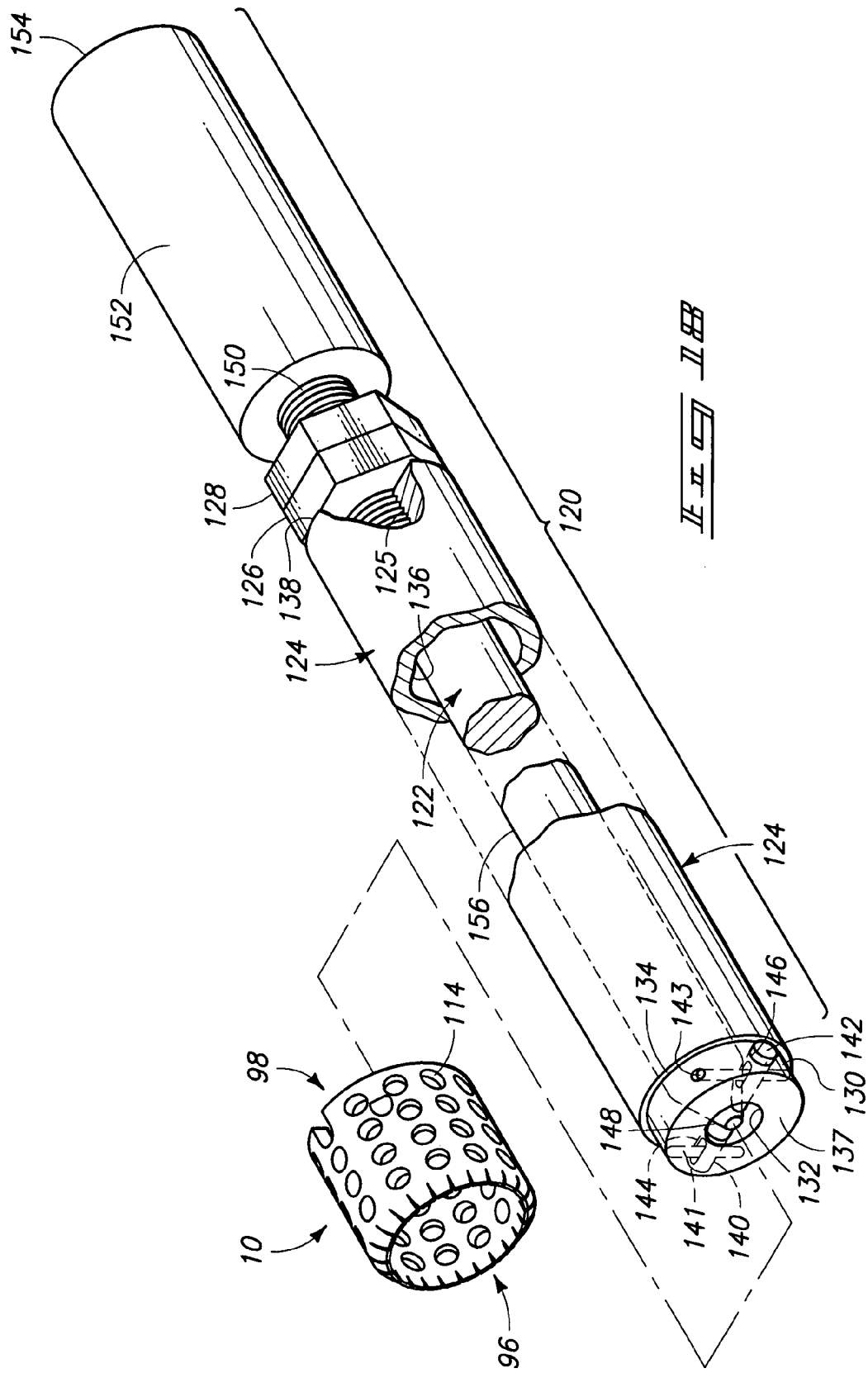

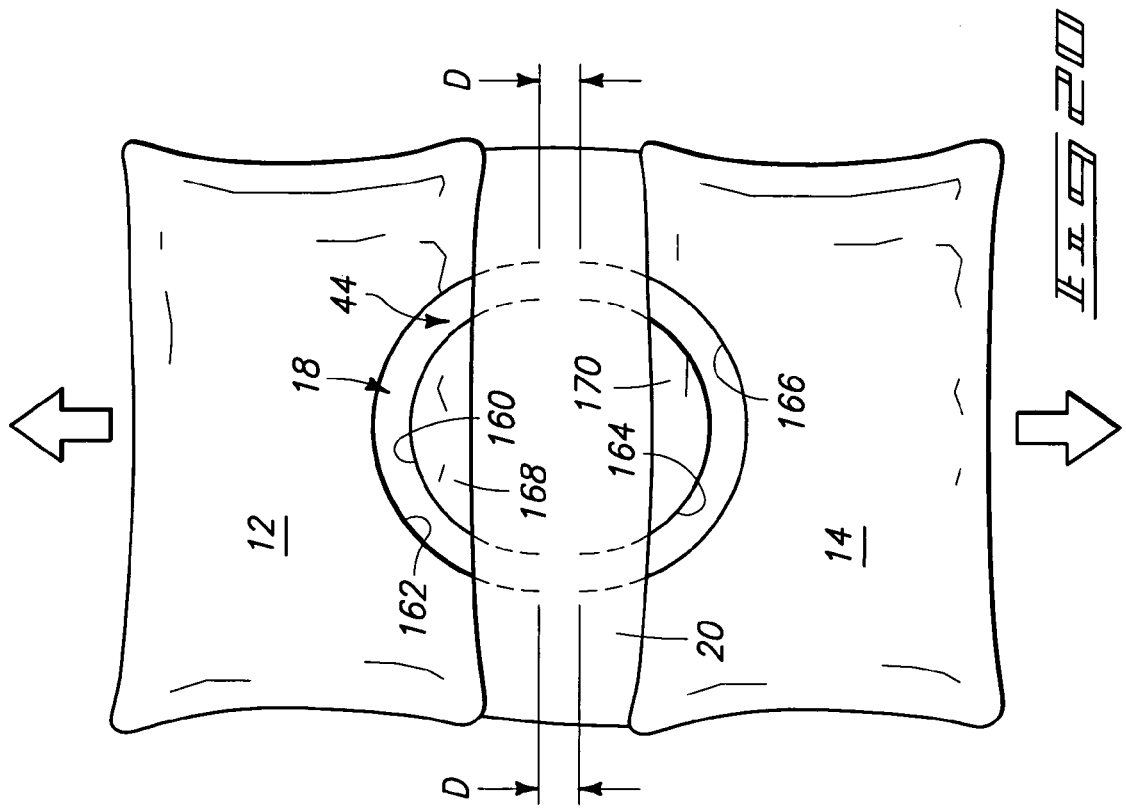
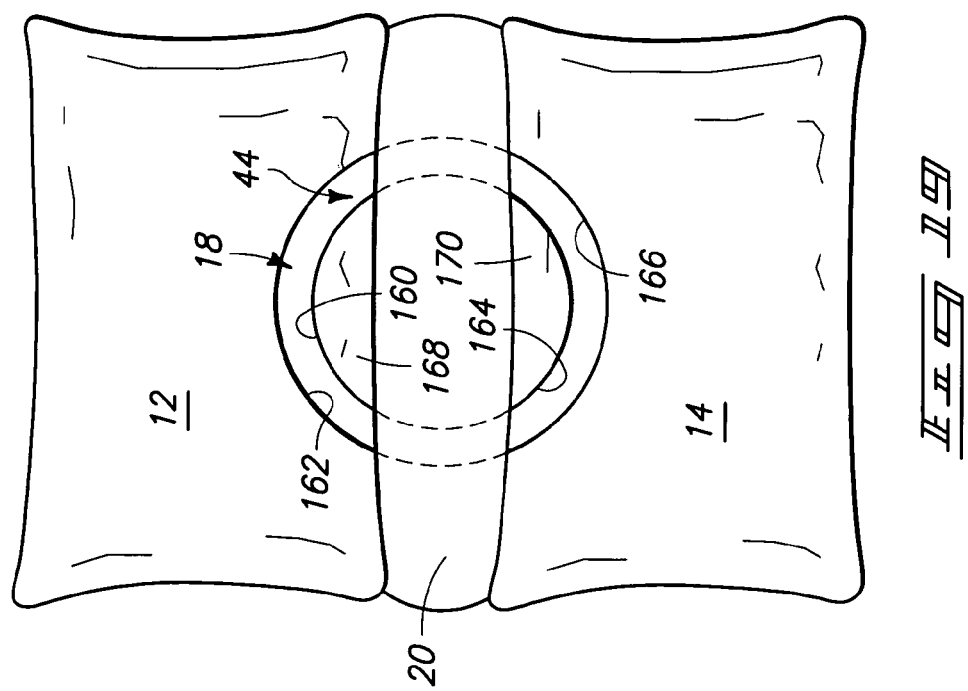

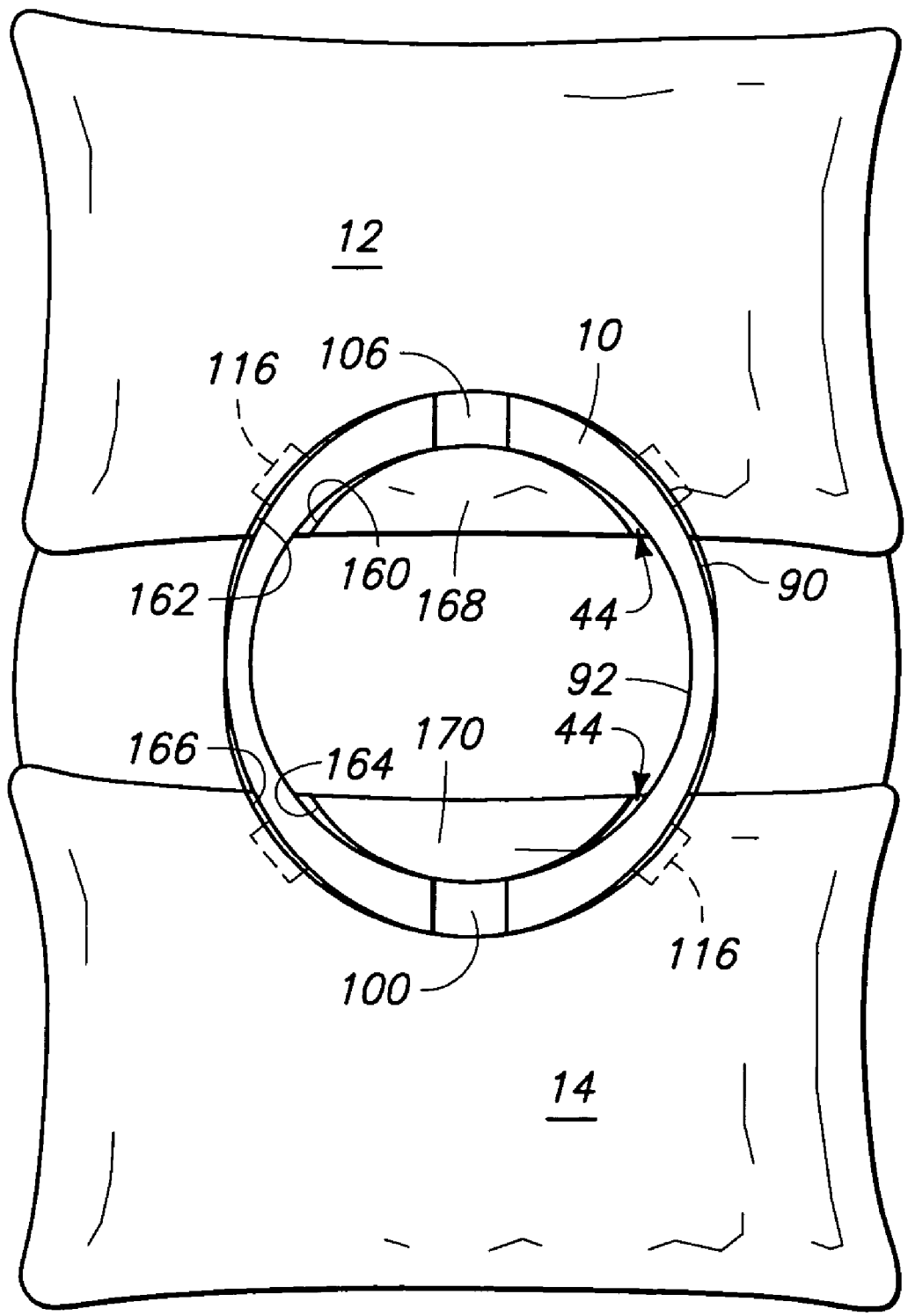

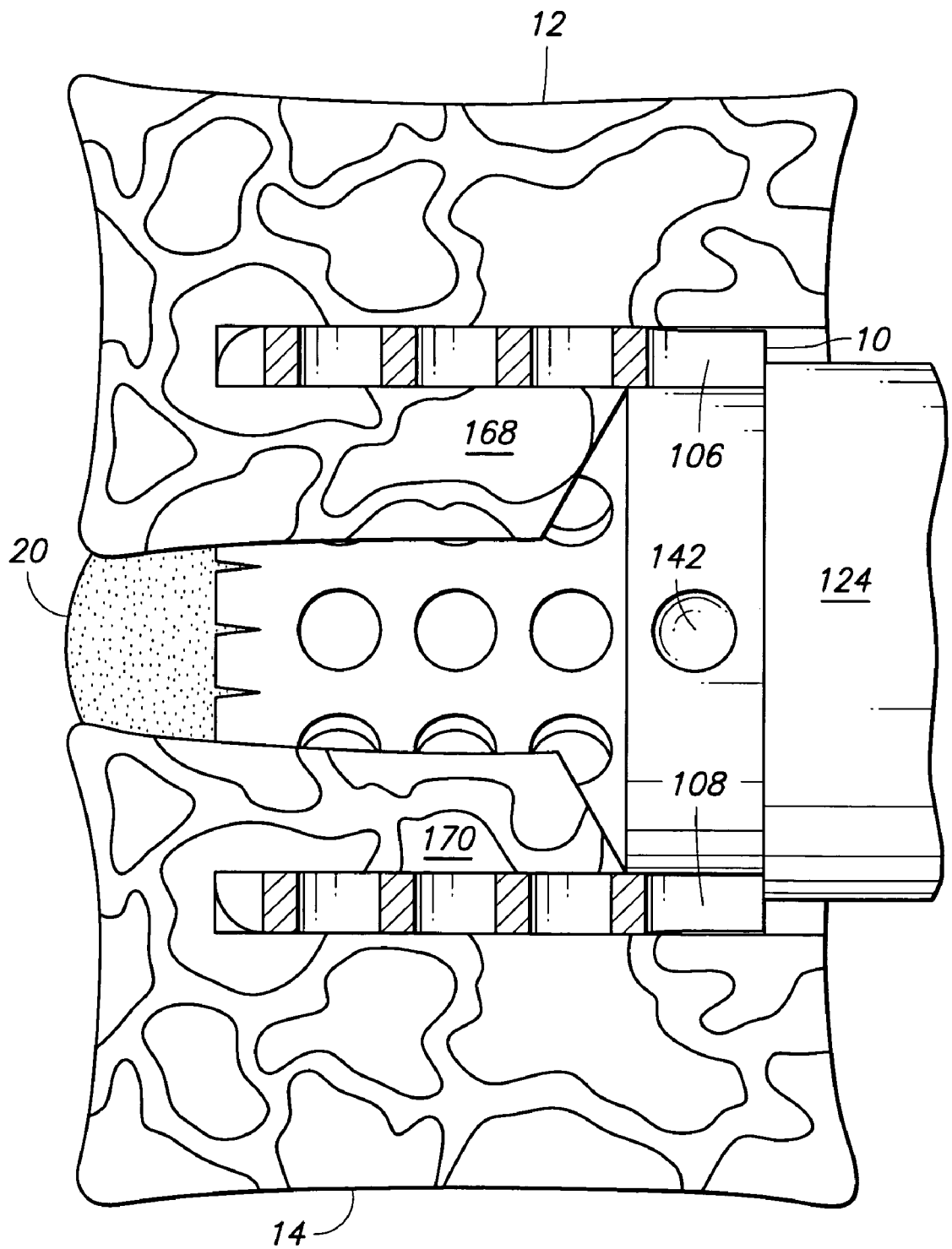

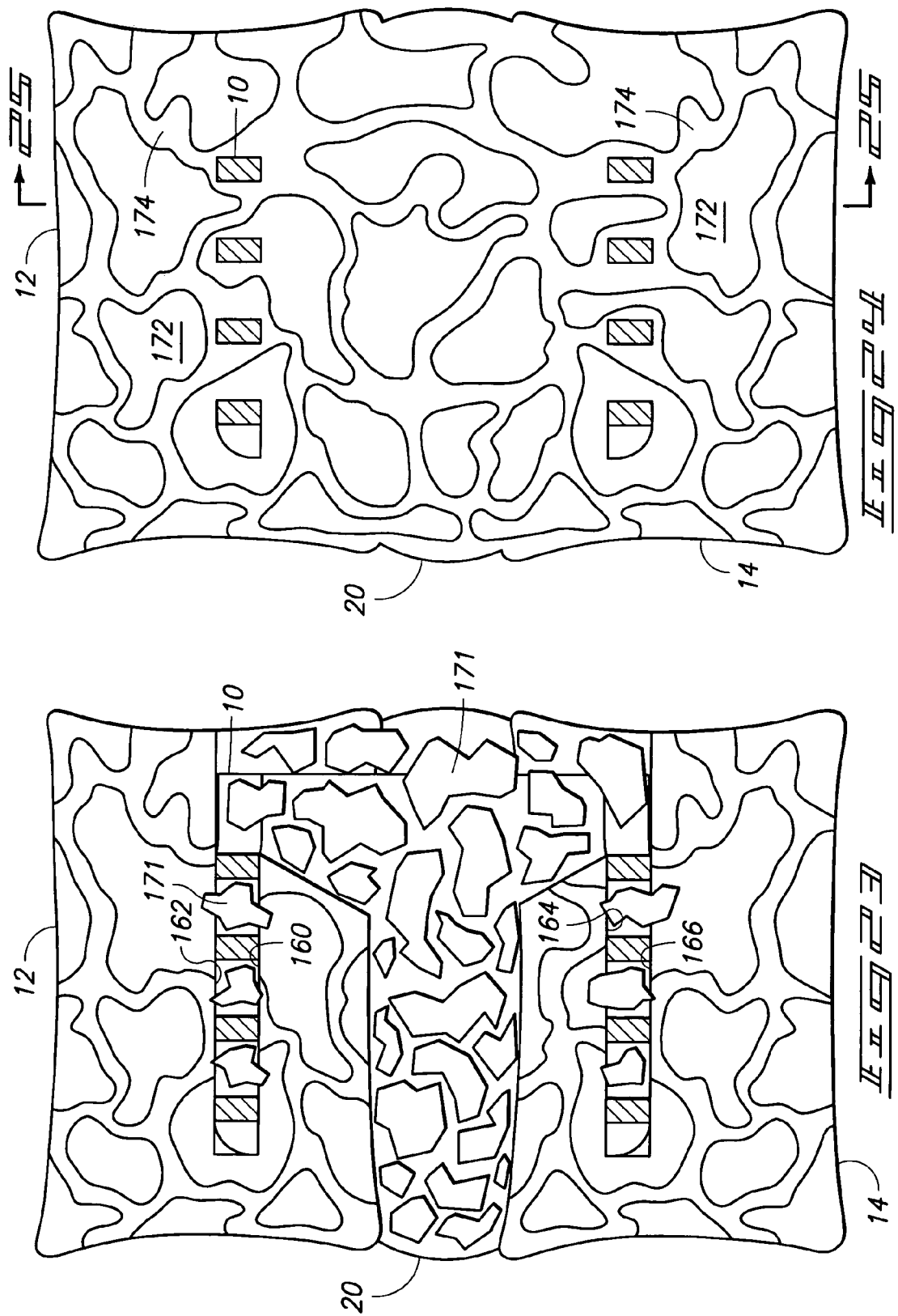

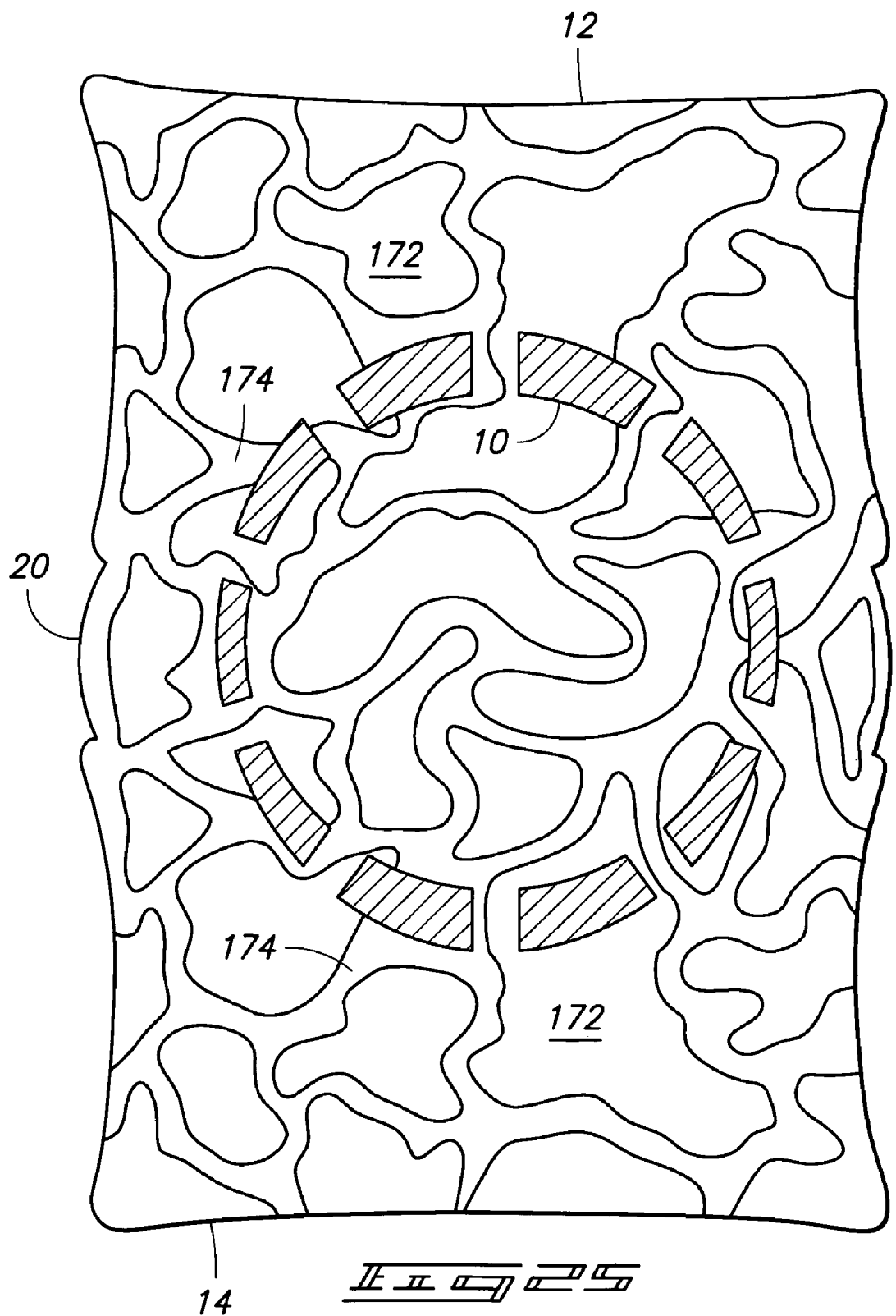

APPARATUS AND METHOD FOR PREPARING A SPINAL IMPLANT SURGICAL SITE FOR RECEIVING A SPINAL FUSION IMPLANT

RELATED PATENT DATA

This continuation application claims the benefits of U.S. patent application Ser. No. 10/775,837, which was filed Feb. 9, 2004, now abandoned entitled "Bone Joining Implant With Retaining Tabs", which in turn was a continuation of U.S. patent application Ser. No. 10/039,384, filed Dec. 31, 2001, and issued Feb. 10, 2004 as U.S. Pat. No. 6,689,167 B2, entitled "Method of Using Spinal Fusion Device, Bone Joining Implant, and Vertebral Fusion Implant", which in turn was a divisional of U.S. patent application Ser. No. 09/179,920, filed Oct. 27, 1998, and issued Apr. 16, 2002 as U.S. Pat. No. 6,371,986, entitled "Spinal Fusion Device, Bone Joining Implant, and Vertebral Fusion Implant", all of which are incorporated by reference herein.

TECHNICAL FIELD

This invention pertains to surgical joining of bone bodies, and more particularly to instruments, implants and methods for self-alignment, instant fixation, distraction, and staged bone fusion or arthrodesis of bone bodies, such as spinal vertebrae.

BACKGROUND OF THE INVENTION

This invention was specifically developed for the surgical joining of bone bodies, such as the fusing of contiguous spinal vertebrae so as to stabilize and prevent relative motion often resulting from a degenerative disc condition. Although the immediate effort leading to this disclosure is directed toward the lumbar, thoracic and cervical spine (anterior or posterior in approach), the described vertebral implants for immediate fixation and staged stabilization leading to arthrodesis (bone fusion) of bone bodies may be used in a bone fracture or osteotomy to fuse together resulting bone bodies, and across one or more joints or articulations. Furthermore, the implants may be used in the lumbar, thoracic and cervical spine.

The use of fixation plates and screws to hold together disunited bone bodies has long been known to facilitate arthrodesis or bone-to-bone union, such as bone fusion, and healing of fractured bones. Typically, the separate bone bodies are formed when a single bone fractures, requiring bone reunion. Plates are secured across a fracture region with screws, joining together the bone bodies. The plates hold the bone bodies together in proximate relation, facilitating bone growth and fusion therebetween. In this manner, the bone bodies are supported in close proximity, or in direct contact which facilitates fusion therebetween. For cases where it is impossible to fixture together bone bodies internally of a patient's skin, external fixation is used. For external fixation, threaded pins are rigidly secured into each bone body. The pins, which extend outwardly of a patient's skin, are fixtured together with an external fixation device, placing the bone bodies in adjacent proximate position to promote healing therebetween. However, these techniques are not practical for certain joints such as joints formed between spinal vertebrae. Therefore, a significant number of stabilizing implants have been designed for joining together contiguous vertebrae.

One early technique for achieving arthrodesis between adjacent vertebrae across a joint or articulation is the well-known Cloward Technique for use in the human cervical spine. A solitary dowel of bone is tapped into place in a prepared circular bed that is smaller than the dowel of bone. The dowel acts as a wedge, distracting the surrounding soft tissues of the joint, and separating the bone bodies or vertebrae joined there along. The intervertebral disc substantially comprises the soft tissues of the joint. The dowel of bone is inserted, or wedged into place, providing its own stability by putting an annulus of the disc on stretch. Additionally, simple friction of the inserted dowel between adjacent vertebral bodies stabilizes axial dislocation. However, a second surgical procedure must be performed to extract or harvest the dowel of bone, substantially adding trauma to the procedure, increasing costs, as well as increasing the threat of infection to the patient. Alternatively, bank bone from human donors can be used, but bank bone is less osteogenic and may introduce infection, or even transmission of Acquired Immune Deficiency Syndrome (AIDS) or hepatitis. Furthermore, bone morphogenic protein, hydroxy apatite, or other bone stimulating material may be utilized. Additionally, there has been a need to ensure the implant remains axially secured which has lead to further developments.

A step forward from the Cloward Technique was provided by Bagby (U.S. Pat. No. 4,501,269) wherein a metal dowel uses the same principle. A perforated cylindrical hollow implant is inserted between prepared surfaces across a vertebral joint. The inserted implant immediately stabilizes the joint by spreading the bony surfaces apart in wedged opposition to surrounding tissue. This initial stabilization is more substantial because a metal dowel, unlike a bone dowel, will not be absorbed or fatigue in use. Over time, fusion occurs through and around the implant which is filled with bone fragments. Use of the metal dowel eliminates the need for a second operation to harvest a dowel of bone. Bone fragments to be inserted in the implant are retrieved during preparation of the circular beds in each vertebra. Furthermore, such a metal implant avoids the disadvantage of having to use a bone bank to obtain donor bone. The Bagby implant described in U.S. Pat. No. 4,501,269 has a smooth outer surface, interrupted only by numerous openings or fenestrations through which bone ingrowth and through growth can occur. Ends of the implant are substantially closed, with one end receiving an end cap such that bone fragments are contained therein. Bone morsels or bone grafts are typically harvested when preparing the circular bed in each vertebra, after which they are placed into the fenestrated metal cylindrical implant. The Bagby implant is then driven or tapped into place in a manner similar to the placement of Cloward's Bone Dowel, which was solely directed for use in the cervical spine. However, the original Bagby implant relies completely upon stretch of the annulus to stabilize the vertebrae during bone remodeling and fusion.

Improvements have also been made to "Cloward's Technique" wherein two dowel bone grafts are posteriorly inserted (Wiltberger's Technique) between adjacent lumbar vertebral bodies. Furthermore, threaded surfaces have been added to such bone grafts in order to keep the grafts in place (Otero-Vich German Application Number 3,505,567, published Jun. 5, 1986). More recently, a number of U.S. patents have proposed combining the threaded features from threaded bone grafts with a metal implant, resulting in rigid threaded implant structures for placement between adjacent spinal vertebrae.

One threaded metal fusion implant disclosed in Michelson (U.S. Pat. No. 5,015,247) provides a cylindrical fusion implant having an outer diameter sized larger than the space between adjacent vertebrae to be fused. Threads provided on the exterior of the member engage the vertebrae to axially secure the implant therebetween. The implant has a plurality of openings configured along the cylindrical surface to promote bone ingrowth. However, the threads per se of the implant do not function as a fastener to fix together the adjacent vertebral bodies. Instead, the implant functions as a wedge, imparting a distraction force across the disc which stabilizes the articulation formed therebetween by stretching the annulus of the disc. In fact, the threaded implant relies solely on the annulus to provide stabilization between the vertebrae, in direct response to wedge-induced distraction created therebetween. Distraction of the annulus stabilizes the two vertebrae, enabling ingrowth to later occur within the implant. Therefore, through-growth and fusion (arthrodesis) occur between the adjacent vertebrae subsequent thereto depending on the immobilizing potential of an intact healthy annulus which may or may not be present.

Several additional problems result from the provision of threads on a cylindrical fusion implant. One problem results in that threads take up additional space which makes implantation in areas having limited anatomical space very difficult, such as in the posterior approach in the lumbar spine. Additionally, the threads effectively make the wall thickness greater which further separates bone provided inside the implant with bone provided outside the implant, which can delay initial bone union.

For bone fusion to occur with any of the above devices, the invasion of new delicate blood vessels from the adjacent healthy bone is necessary for the creation of new living interconnecting bone. Where complete stabilization does not occur instantaneously upon implantation, motion can disrupt the ingrowth of delicate blood vessels. Disruption of the vessels then restricts or even prevents bone healing therebetween. The same problem occurs with any of the above-mentioned implant techniques, including the threaded techniques of Otero-Vich and Michelson. Even when the annulus is completely on stretch, the threads per se of these constructions do not function in the manner of conventional screws, extending through one object and into another. Namely, they do not function to fasten together adjacent bodies by coaction of the implant with each body. For example, the threads merely act as a series of ridges that engage with each adjacent bone body, while the implant body functions as a wedge. The implant distracts apart the vertebral bodies which stretches the annulus, and stabilizes the articulation as a consequence thereof, while the thread functions solely to prevent axial dislodgement. Furthermore, the presence of threads requires the implant to be screwed in place via a torquing process, instead of tapping the implant directly into position.

Hence, some recent designs have resulted in an implant that produces immediate fixation per se between bone bodies following insertion and independent of the annulus. Such designs show promise particularly for cases where the annulus structure is substantially or completely weakened or damaged at surgery. Where the annulus is damaged so significantly as to lose structural integrity, the wedge-effect of prior art threaded implants will not produce any distraction forces across the annulus. Also, when the implant is used to arthrodese and change angulation, a healthy annulus cannot be totally corralled to be placed on stretch. As a result, there is no form of stabilization or fastening between bone bodies sufficient to enable the occurrence of arthrodesis therebetween when the annulus is weakened or inadequate. Additionally, there exist additional shortcomings with such recent designs as discussed below.

One such design that produces immediate fixation is disclosed in Bagby (U.S. Pat. No. 5,709,683) as a bone joining implant having a spline or undercut portion that engages in assembly with each bone body to be joined. However, such design requires the preparation of bone beds that are engaged in interlocking relation with a bone bed engaging portion provided by such undercut portions.

Many of the previously described implants can be inserted between vertebrae while such vertebrae are distracted with a distraction tool. One such tool uses a threaded pin which is inserted laterally into each bone body, with such pins being rigidly secured therein. Such tool distracts the vertebrae by separating the pins and vertebrae which stretches the annulus. A drill is then used to drill out bone beds within the vertebrae, after which the implant is inserted therein. However, such procedure does not always impart sufficient distraction and takes time and space to implement.

Yet another group of implant designs provide distraction between adjacent vertebrae, including U.S. Pat. No. 5,665,122 to Kambin and U.S. Pat. No. 5,702,455 to Saggar. Kambin teaches an expandable intervertebral implant formed from several components that cooperate with an expansion screw to distract adjacent vertebral bodies by expanding two of the cage components relative to one another. However, such design is formed from several discrete components that are movably fastened together and which are susceptible of loosening and misadjusting within a patient. Saggar teaches a spine stabilizing prosthesis that is inserted within a cavity between vertebrae. Such design forms a jacking screw adjustment member that expands apart a pair of bearing members, each engaged with a respective vertebra. However, such design is illustrated in use as being inserted within a vertebral cavity that is formed by removal of a portion of a vertebra such as is formed by a corpectomy.

Therefore, there is a present need to provide an implant device that instantly fastens bone bodies together upon implantation, enhances arthrodesis by encouraging bony fusion adjacent the implant, and imparts distraction between adjacent bone bodies during insertion. There is also a need to provide such a device that facilitates staged stabilization leading to bone fusion, in a manner that is relatively simple, more reliable, less complicated, has fewer parts, and leads to quicker and more thorough bone fusion and remodeling therebetween. The final stage of bone fusion through and around the implant substantially eliminates any need for the implant to maintain the fusion, thus allowing the bone union to provide primary support therebetween.

SUMMARY OF THE INVENTION

In accordance with an aspect of the invention, an apparatus is provided for preparing a spinal implant surgical site for receiving a spinal fusion implant. The apparatus includes a drive shaft, a handle, and a hollow, cylindrical cutting body. The handle is carried by the drive shaft, the hollow, cylindrical cutting body is provided at a leading end of the drive shaft. The cylindrical cutting body has an open leading end, a plurality of circumferentially spaced-apart cutting teeth provided on the open leading end, and a plurality of circumferentially spaced-apart gullets each provided between an adjacent pair of the cutting teeth.

In accordance with one aspect of the invention, a bone joining implant comprises a tubular body having an open leading end, an open trailing end, and a central aperture; the open leading end communicating with the central aperture and configured to entrap a bone projection from each of a pair of adjacent bone bodies being joined together. The bone projection is integrally formed from each bone body being joined, and the implant houses bone graft material therein. The bone projections and bone graft material cooperate to enhance arthrodesis. Such implant directly and instantly stabilizes adjacent bone bodies by entrapping the bone projections.

In accordance with a second aspect of the invention, a vertebral interbody implant comprises a tubular body having an oblique outer surface and a cylindrical inner surface, and a tapered portion extending from a cylindrical leading end between the inner surface and the outer surface. The cylindrical leading end is sized to be received within bone beds of adjacent vertebrae being joined, and the tapered portion operative to self-distract the vertebrae during insertion of the oblique outer surface therebetween. The tapered portion, in combination with the oblique outer surface, imparts indirect stabilization by commanding an annulus between the adjacent bone bodies to tighten or stretch in response to distraction of the adjacent bone bodies.

In accordance with a third aspect of the invention, a tubular implant contains an aperture extending completely through the implant having a substantially continuous inner diameter which facilitates x-ray evaluation of bone healing within the implant, following implantation and arthrodesis. Particularly, such aperture facilitates evaluation extending in a direction along the axis of the tubular implant, generally in an anterior to posterior direction.

In accordance with a fourth aspect of the invention, a single tubular body implant is provided for implantation between the pair of bone bodies. Such tubular implant caters to a reduced amount of surgery in that a single implant serves the surgical purpose of two implants, in selected cases.

In accordance with a fifth aspect of the invention, a tubular implant includes a tubular body having an oblique outer surface and a cylindrical inner surface that is configured to be received in conforming implantable relation with a pair of bone bodies that are formed from a single cylindrical cut taken between adjacent bone bodies. Upon distraction, the cylindrical cut forms an obliquity between the adjacent bone bodies which conforms in substantially compliant fit-up with the oblique outer surface of the tubular implant. Such conforming fit-up increases frictional stabilization between adjacent bone bodies by generating a larger contact surface area therebetween. Furthermore, the oblique outer surface mates with such bone bodies in a manner that imparts a degree of lateral stabilization so as to prevent lateral movement at the adjoining interfaces.

In accordance with a sixth aspect of the invention, a tubular implant is provided with an open leading end and a central aperture in a manner to entrap intact bone projections extending from each of a pair of adjacent bone bodies. Such entrapment provides immediate, or instant, fixation between the adjacent bone bodies in a manner that caters to retention of the local bone bodies via the intact bone projections. Furthermore, bone graft material, or chips, are provided within the interior of the tubular implant so as to provide osteogenic material that is placed inside the implant. Such osteogenic material is preferably generated during preparation of the bone beds, which eliminates the need to perform additional surgeries for obtaining foreign bone graft material from other locations on a patient, or from another patient.

BRIEF DESCRIPTION OF THE DRAWINGS

Preferred embodiments of the invention are described below with reference to the following accompanying drawings.

FIG. 13 is a perspective view taken from the driven end of the vertebral interbody implant of FIG. 12;

FIG. 14 is a side view of the vertebral interbody implant of FIG. 12;

FIG. 15 is a leading end view of the vertebral interbody implant of FIG. 12;

FIG. 16 is a driven end view of the vertebral interbody implant of FIG. 12;

FIG. 17 is an unrolled plan view of the outer peripheral surface of the vertebral interbody implant of FIGS. 12-16;

FIG. 18 a perspective view illustrating an implant insertion tool usable for inserting the implant of FIGS. 12-16;

FIG. 19 is a simplified frontal view illustrating a pair of vertebrae that have bone beds prepared according to the steps depicted in FIGS. 1-11 comprising a cylindrical kerf;

FIG. 20 is a simplified frontal view illustrating the vertebrae of FIG. 19 in a distracted position corresponding to the position generated by inserting the implant of FIGS. 12-16;

FIG. 21 is a simplified frontal view illustrating the vertebrae of FIG. 20 in a distracted position caused by inserting Applicant's implant of FIGS. 12-16;

FIG. 22 is a simplified sagittal view taken along the centerline of the implant of FIGS. 12-16;

FIG. 23 is a surgical time simplified sagittal view of the implant of FIG. 22 received within the prepared bone beds of adjacent vertebrae and containing bone fragments immediately following implantation;

FIG. 24 is a healed time simplified sagittal view of the implant of FIG. 22 received within the prepared bone beds of adjacent vertebrae and illustrating the vertebra following bone remodeling and reorganization and showing arthrodesis;

FIG. 25 is a coronal view of the implant and healed bone comprising vertebrae and taken along line 25-25 of FIG. 24 and showing arthrodesis;

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

Figure 1:
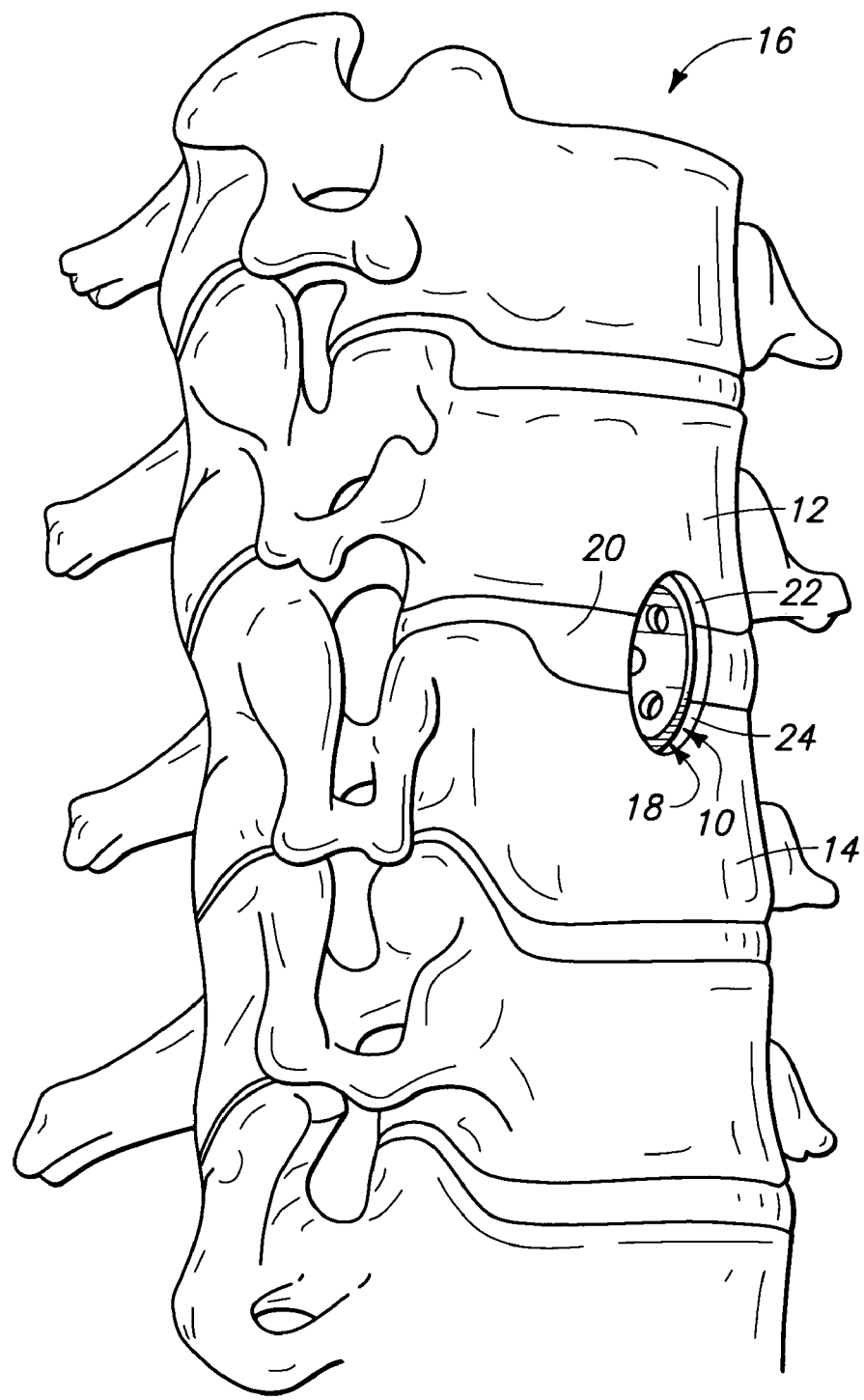
FIG. 1 is a perspective view of a vertebral structure showing a vertebral interbody implant embodying this invention.
Figure 2:
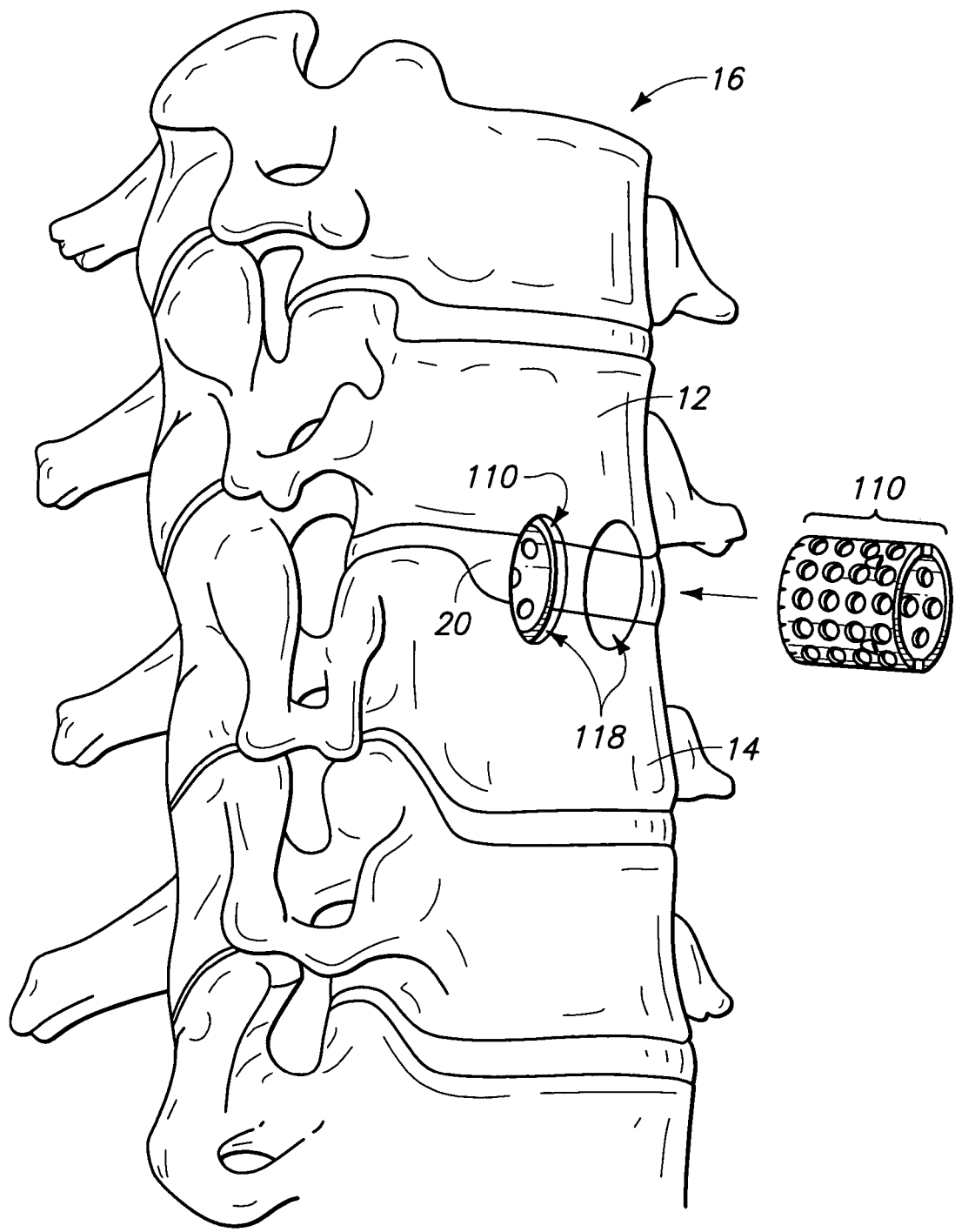
FIG. 2 is a perspective view of a vertebral structure showing a pair of vertebral interbody implants, similar to the implant depicted in FIG. 1, embodying this invention.

A preferred embodiment bone joining implant in accordance with the invention is first described with reference to FIGS. 1, 12-18 and 21-25. Such an implant is described further below with respect to an open-ended vertebral interbody implant having instant fixation in the form of a leading open end and self-distraction features in the form of a cylindrical inner surface and an oblique outer surface. The fixating and self-distracting implant is designated in FIGS. 1, 12-18 and 21-25 generally with reference numeral 10. An alternative implementation comprising a pair of somewhat smaller sized implants 110 are depicted in FIG. 2. Yet another alternative implementation comprises a substantially cylindrical tubular implant 210 depicted in FIGS. 26 and 27.

As shown in FIGS. 1, 12-18 and 21-25, implant 10 comprises a rigid, unitary body having a cylindrical leading edge 86 and an oblique outer surface 90, with an open leading end 96 (see FIGS. 12-16). As shown in FIG. 1, implant 10 is inserted within an aperture 18 formed between a pair of adjacent vertebral bodies 12 and 14 within a vertebral column 16.

As shown in FIG. 1, aperture 18 is prepared within vertebral bodies 12 and 14, and disc 20, according to the procedure and tools depicted in FIGS. 5-11 described below in further detail. Aperture 18 forms a pair of vertebral bone bodies 22 and 24 that are formed to have a cylindrical configuration comprising a cylindrical kerf 44 (see FIG. 19). A leading cylindrical end of implant 10 is inserted into aperture 18, causing annulus 20 to distract as implant 10 is inserted therein (see FIGS. 19-21 below). A leading open end 96 (see FIG. 12) of implant 10 entraps an intact living bone projection 168 and 170 on each respective vertebral body (see FIGS. 19-22) which imparts immediate fixation between adjacent vertebral bodies 22 and 24 upon implantation.

More particularly, vertebrae 12 and 14 comprise neighboring bone bodies of a vertebral column 16 (see FIG. 1). A resilient articulation or joint is formed between vertebrae 12 and 14 by a disc 20 extending between vertebrae 12 and 14. Anatomically, the disc is made up of a central nucleus pulposus and an outer encircling annulus. The annulus and nucleus pulposus are composed of laminae of fibrous tissue and fibrocartilage. The nucleus pulposus, located at the center of the disc, comprises a soft, pulpy, highly elastic substance. The annulus is formed from laminae of fibrous tissue extending in criss-crossing fashion to encircle the nucleus pulposus. Additionally, the intervertebral disc is adherent, by its cephalad and caudad surfaces, to a thin layer of hyaline cartilage that covers the top and bottom surfaces of adjacent vertebrae. In a healthy patient, adjacent vertebrae 12 and 14 are spaced apart by disc 20. However, degenerative disc disease and localized trauma can cause degradation or complete loss of the soft tissue components between neighboring vertebrae. For example, the annulus can partially or completely tear which can seriously degrade the structural condition of the articulation. Additionally, fluid can escape from the nucleus pulposus. When any of the above happens, vertebrae 12 and 14, loaded by the normal weight bearing of a patient, are pressed into closer adjoining positions, which can result in pinching of nerves that extend from between vertebrae of the spinal column (not shown).

Therefore, there is a need to recover the disc spacing provided by a normal healthy disc 20 by way of inserting implant 10. Furthermore, there is a need to provide implant 10 with a fixation that instantly interlocks adjacent vertebrae 12 and 14 together upon being implanted. Furthermore, there is a need for such an implant 10 that imparts distraction to disc 20 upon insertion and that facilitates staged stabilization resulting in arthrodesis to occur between the vertebral bodies, following initial implantation. Even furthermore, there is a need to instantly fix adjacent vertebrae together since relative motion can otherwise cause pinching of nerve tissue.

As a result, implant 10 can be inserted, preferably in a central location between adjacent vertebrae 12 and 14 of patients who have bad, ruptured or degenerative discs. A pair of somewhat smaller sized laterally positioned implants may also be used in chosen cases, as shown in FIG. 2. Furthermore, implant 10 can be axially oriented anterior to posterior, or even laterally. In summary, implants 10 are adapted for implantation between prepared bony surfaces or beds 22 and 24 and across the articulation formed by disc 20. A typical implantation might involve placement of one or more implants 10 as required in order to stabilize and fix the joint during bone ingrowth and through-growth of the implant structure. Bone growth is also accomplished outside of and surrounding the implant.

FIG. 2 illustrates an alternative implementation comprising a pair of laterally positioned implants 110. Implants 110 are essentially identical to implant 10 (of FIG. 1), but are sized smaller in dimension. Such implementation enables correction of lateral spinal curvatures by inserting a laterally positioned pair of implants 110 having different outer dimensions into similarly sized bone beds between adjacent vertebrae. Such dual implant implementation also imparts additional stability across disc 20 over that provided by the single implant implementation depicted in FIG. 1.

However, such dual implant implementation uses individual implants 110 that are sized smaller than the single implant 10 of FIG. 1. As a result, such dual implant implementation uses smaller sized apertures 118 which do not invade as much cancellous bone as the apertures 18 (see FIG. 1) for the larger sized single implant implementation of FIG. 1. A solitary implant 10 as shown in FIG. 1 invades cancellous bone since aperture 18 has a larger diameter. In contrast, the smaller sized dual implants 110 of FIG. 2 tend to invade mostly cortical bone on the end plates. However, cancellous bone is more desirable for bone growth during staged bony fusion since cancellous bone is more osteogenic than cortical bone. New growth bone, or callus bone, comprises soft cancellous bone that only becomes hard (cortical) over time via action of Wolff's Law of maturity.

Figure 3:
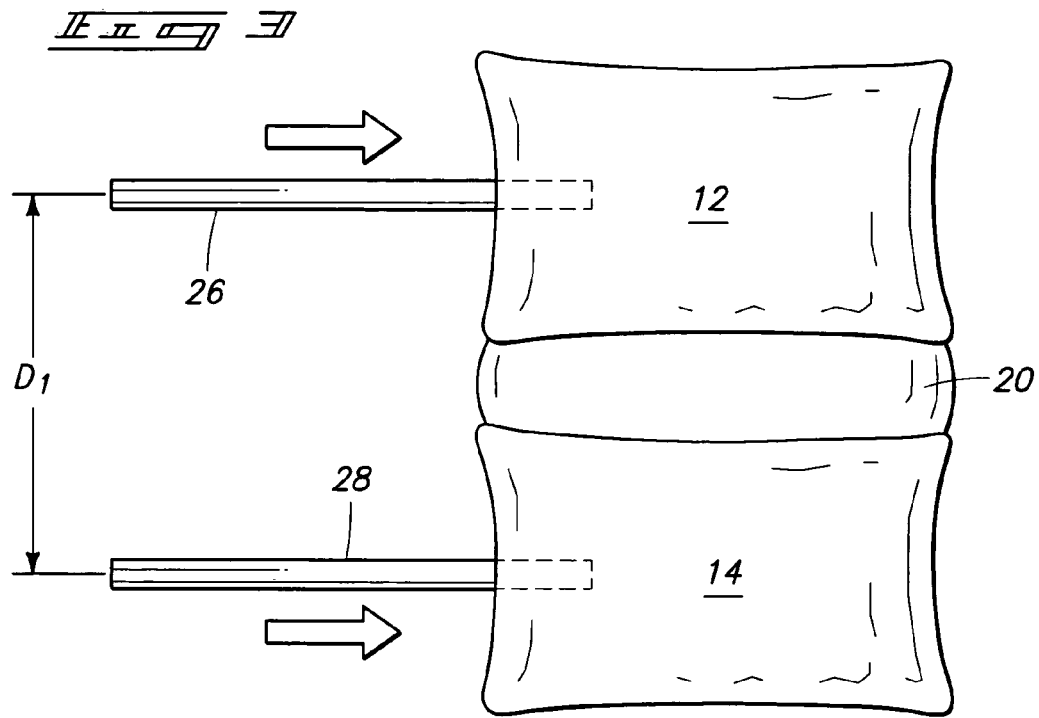
FIG. 3 is a simplified frontal view illustrating a pair of adjacent vertebral bodies prepared with distraction pins.
Figure 4:
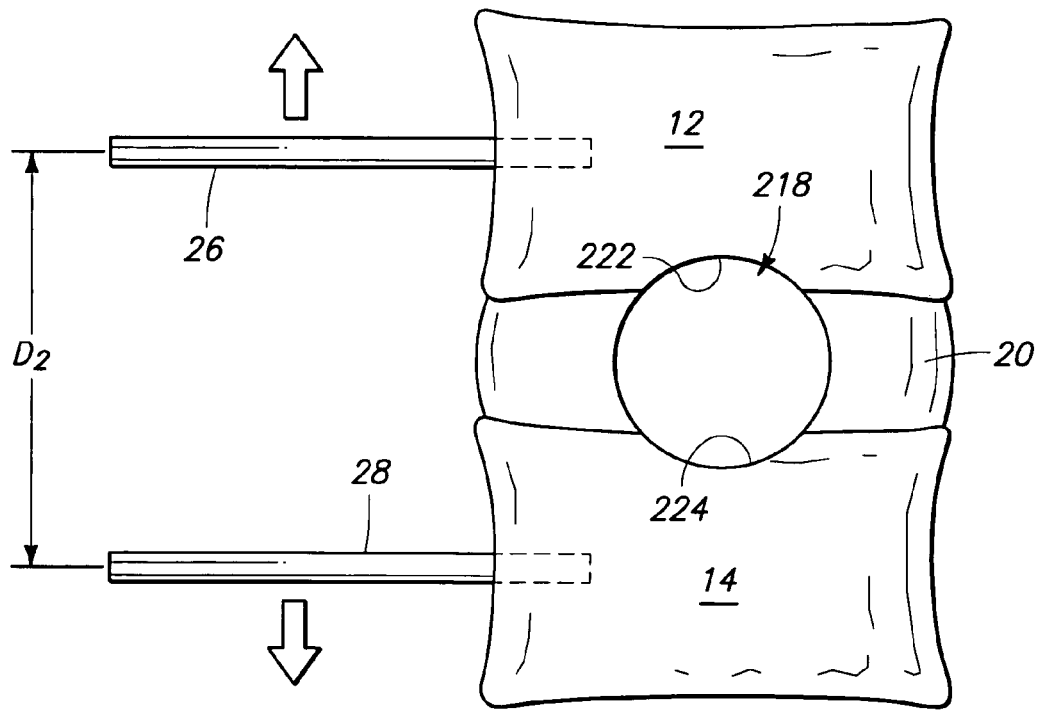
FIG. 4 is a simplified frontal view corresponding to the view depicted in FIG. 3, and illustrating a pair of adjacent vertebral bodies distracted by a distraction tool (not shown) that applies forces to the distraction pins.

FIGS. 3 and 4 illustrate one technique for distracting an articulation between adjacent vertebral bodies 12 and 14 by placing disc 20 under stretch. Such technique has been used with prior art vertebral interbody implants and fusion cages to impart distraction, after which an aperture 218 (see FIG. 3) is formed in the articulation into which an implant is inserted. However, some relaxation typically occurs to disc 20 following insertion.

In contrast, Applicant's implant depicted in FIGS. 1 and 2 generates self-distraction during insertion. It is understood that Applicant's invention can be implemented in combination with the distraction technique taught in FIGS. 3 and 4 in order to further impart distraction between vertebral bodies 12 and 14 by stretching disc 20.

As shown in FIG. 3, a rigid metal pin 26 and 28 is inserted in a lateral direction into each vertebra 12 and 14, respectively. Pins 26 and 28 are each formed from a cylindrical piece of rigid stainless steel having a threaded leading end (not shown). Such pins 26 and 28 are formed in a manner similar to Harrington rods, but are shorter in overall length. Pins 26 and 28 are threaded into respective apertures that have been pre-cut or drilled into vertebrae 12 and 14, respectively. Preferably, pins 26 and 28 are inserted laterally into vertebrae 12 and 14 such that pins 26 and 28 are rigidly secured in parallel respective relation separated by a spaced apart distance $D_1$.

As shown in FIG. 4, external distraction force is applied between pins 26 and 28 by a distraction tool (not shown) so as to impart distraction between pins 26 and 28 and vertebral bodies 12 and 14. Several tools are understood in the art for distracting apart vertebral bodies. One technique involves modifying a pair of forceps to receive pins 26 and 28. U.S. Pat. No. 4,898,161 to Grundei teaches another variation of a distraction tool comprising a pair of forceps for pushing apart vertebrae. According to the Grundei tool, pins are integrally formed by the forceps for pushing apart adjacent vertebrae when jaws on the forceps are spread apart. Such U.S. Pat. No. 4,898,161 is herein incorporated by reference as showing a distraction tool presently understood in the art. Preferably, pins 26 and 28 are moved apart by the distraction tool so that they remain in parallel relation. Accordingly, vertebral bodies 12 and 14 are moved apart without imparting any relative rotation therebetween. As a result, pins 26 and 28 are distracted to a new spaced apart distance $D_2$. Hence, vertebral bodies 12 and 14 are distracted apart a total distance $D_T = D_2 - D_1$.

Following distraction of vertebral bodies 12 and 14, an aperture 218 is formed cooperatively within vertebral bodies 12 and 14 and further within disc 20 with a drill bit and/or saw. Such aperture 218 forms a pair of bone beds 222 and 224 that receive a prior art vertebral interbody implant.

Optionally, an aperture 18 (as depicted in FIG. 19) can be formed within vertebral bodies 12 and 14 of FIG. 4. Accordingly, distraction $D_T$ can be imparted between vertebral bodies 12 and 14 which is in addition to the self-distraction that is generated by merely inserting implant 10 of Applicant's invention between bodies 12 and 14 as described below with reference to FIG. 21.

FIGS. 5-11 illustrate the preparation of aperture 18 and bone beds 22 and 24 within vertebral bodies 12 and 14, respectively (of FIG. 1). Such figures illustrate one technique for preparing a suitable pair of bone beds within adjacent vertebrae 12 and 14 for receiving implant 10 (of FIG. 1) such that self-distraction and immediate fixation are imparted between vertebral bodies 12 and 14.

Figure 5:
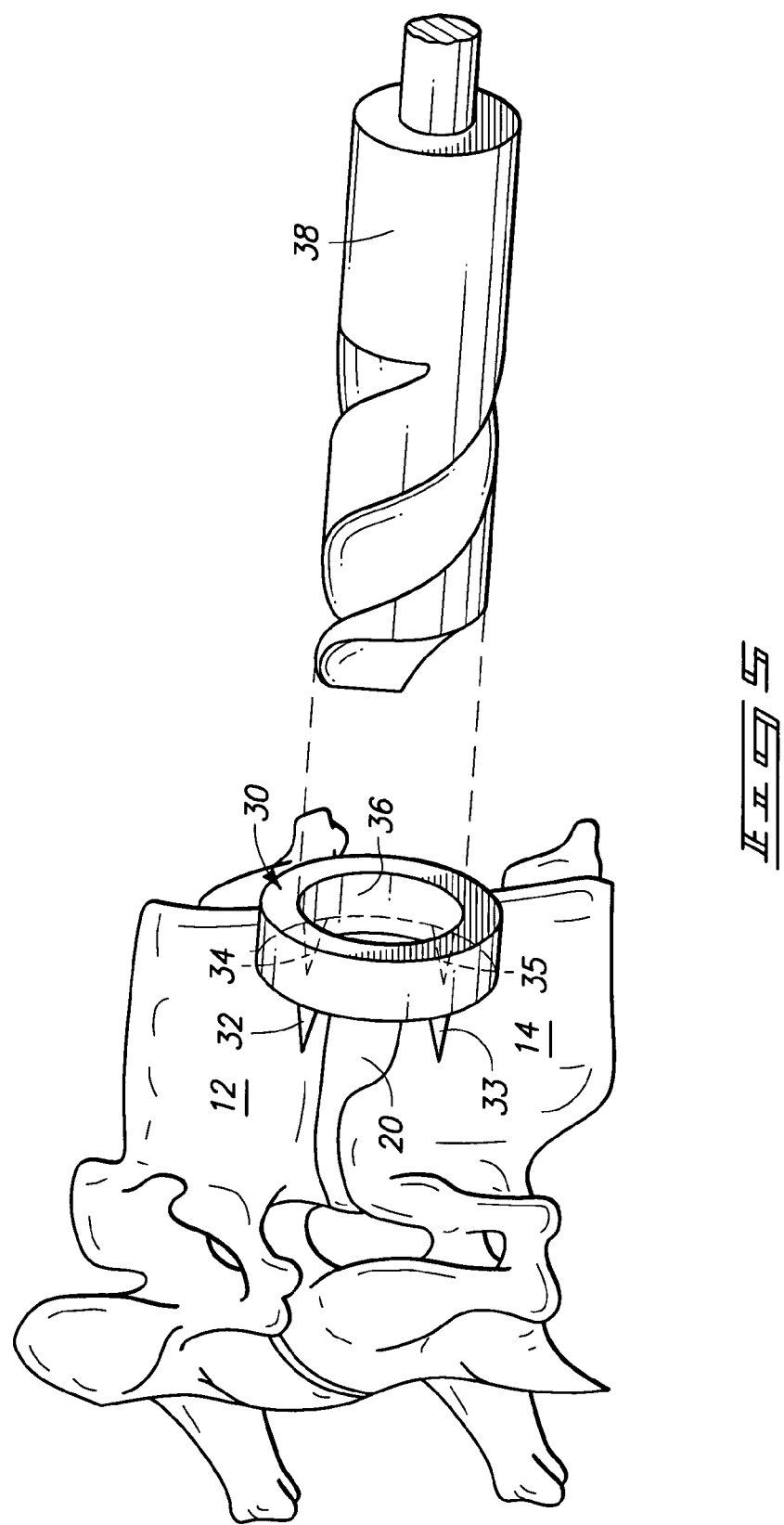
FIG. 5 is a perspective view of a pair of adjacent vertebrae and illustrating a drill guide and drill bit used to form a first bore used to prepare bone beds within the vertebrae.

FIG. 5 depicts a tool guide 30 and a drill bit 38 that are used to drill a bore 40 (see FIGS. 6 and 7) into vertebral bodies 12 and 14 and disc 20. Bore 40 is drilled a sufficient depth into bodies 12 and 14 so as to leave intact living bone projections 168 and 180 (see FIG. 11) having sufficient size to impart instant fixation between bodies 12 and 14 upon insertion of implant 10.

As shown in FIG. 5, tool guide 30 is first tapped into engagement with vertebral bodies 12 and 14 by an alignment drive and hammer (not shown). Sharp fingers or projections 32-35 engage and enter the outer surfaces of bodies 12 and 14 which causes tool guide 30 to be rigidly and securely seated between bodies 12 and 14. In this position, a central bore 36 of tool 30 is aligned in an anterior/posterior direction. Bore 36 is sized to receive and guide a tool bit 38 in an anterior/posterior direction through bodies 12 and 14 and annulus 20.

Figure 6:
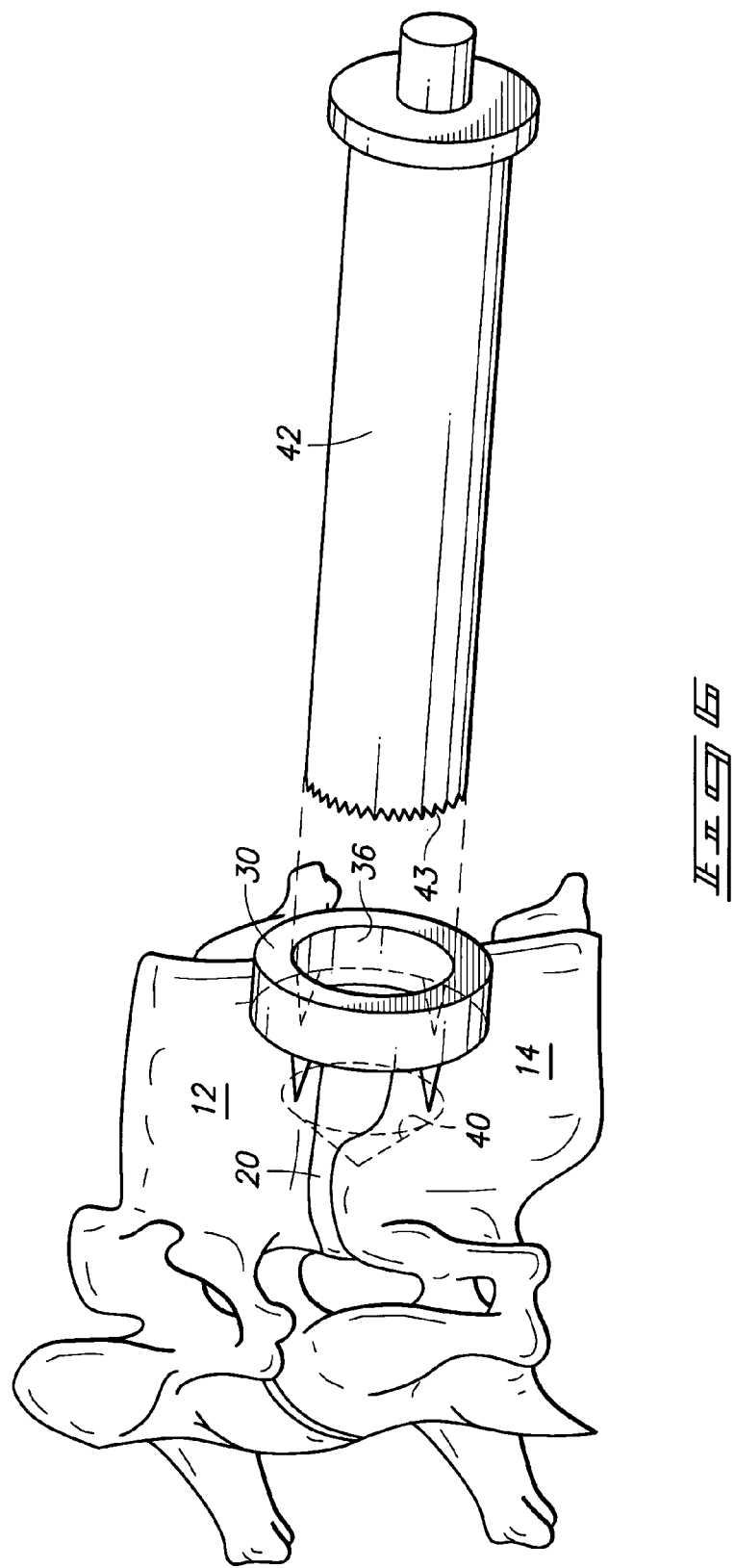
FIG. 6 is a perspective view of the pair of vertebrae of FIG. 5, and illustrating a hole saw used with the drill guide to further prepare the bone beds within the vertebrae by cutting a cylindrical kerf therein.
Figure 7:
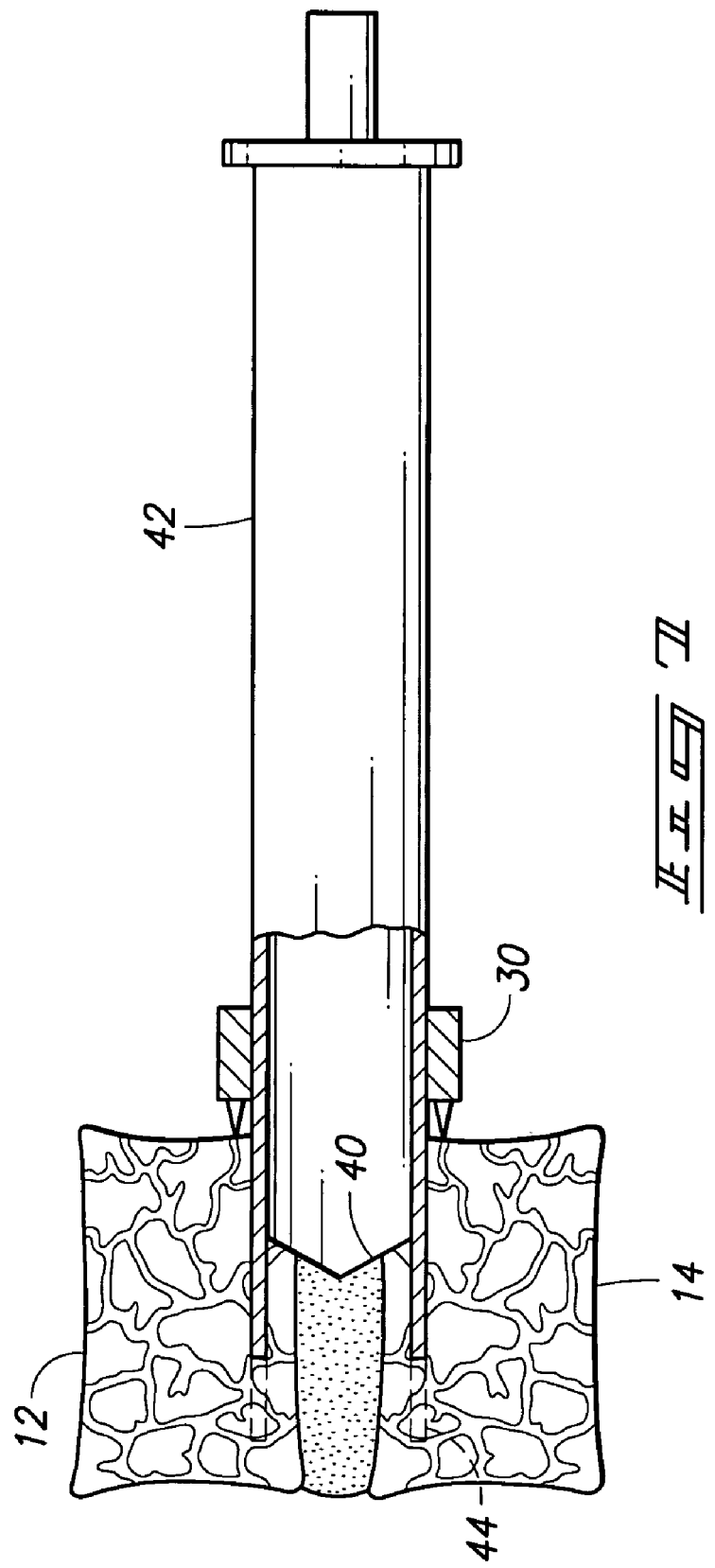
FIG. 7 is a simplified side view illustrating the hole saw of FIG. 6 cutting a cylindrical kerf within the pair of vertebrae.

More particularly, drill bit 38 is driven in rotation by a drill (not shown) so as to cut out bore 40 (see FIG. 7). One suitable drill comprises a Hudson hand-driven manual drill. Alternatively, a power drill can be used to drive drill bit 38. Typically, bore 40 is drilled with sufficient depth into bodies 12 and 14 to extend between 30-70% of the depth of cylindrical kerf 44 as shown in FIG. 7. Kerf 44 is subsequently cut using one or more of the tools depicted with reference to FIGS. 6-11 as described below.

FIG. 6 illustrates a hole saw 42 used in combination with tool guide 30 to form part or all of a cylindrical kerf 44 (see FIG. 7). As illustrated in FIG. 7, hole saw 42 is used to cut a cylindrical groove 68 (see FIG. 9) to a depth approaching 90% of the finished depth of kerf 44. Hole saw 42 is inserted into bore 40 such that a cylindrical groove is cut in axial alignment with bore 40. Thereafter, oscillating cylindrical blade 50 (of FIGS. 8 and 9) is used to cut the remaining depth of cylindrical groove 70 which corresponds to the final depth of kerf 44 as shown in FIG. 9. A hand-driven kerf cleaning/deburring tool 72 is then used to clean debris 84 (see FIGS. 10 and 11) from cylindrical groove 70 which prepares and finishes kerf 44 therein. Optionally, hole saw 42 (of FIGS. 6 and 7) and/or oscillating cylindrical blade 50 can be used to prepared kerf 44. Further optionally, kerf 44 can be formed solely by use of hand-driven tool 72.

As shown in FIGS. 6 and 7, hole saw 42 comprises a hollow saw blade having a shank that is driven in rotation by a drill (not shown). The cylindrical saw blade of hole saw 42 is inserted in bore 36 of tool guide 30 during a cutting operation. Guide 30 directs hole saw 42 to cut in an accurate anterior/posterior direction that is coaxial with bore 40 formed by drill bit 38 (of FIG. 5).

FIG. 7 illustrates hole saw 42 during a cutting operation. According to one implementation, hole saw 42 is used to cut to a depth indicated by cylindrical groove 68 shown in FIG. 9. Subsequently, reciprocating cylindrical blade 50 (of FIGS. 8 and 9) is used to further and substantially form a remaining portion of kerf 44.

Figure 8:
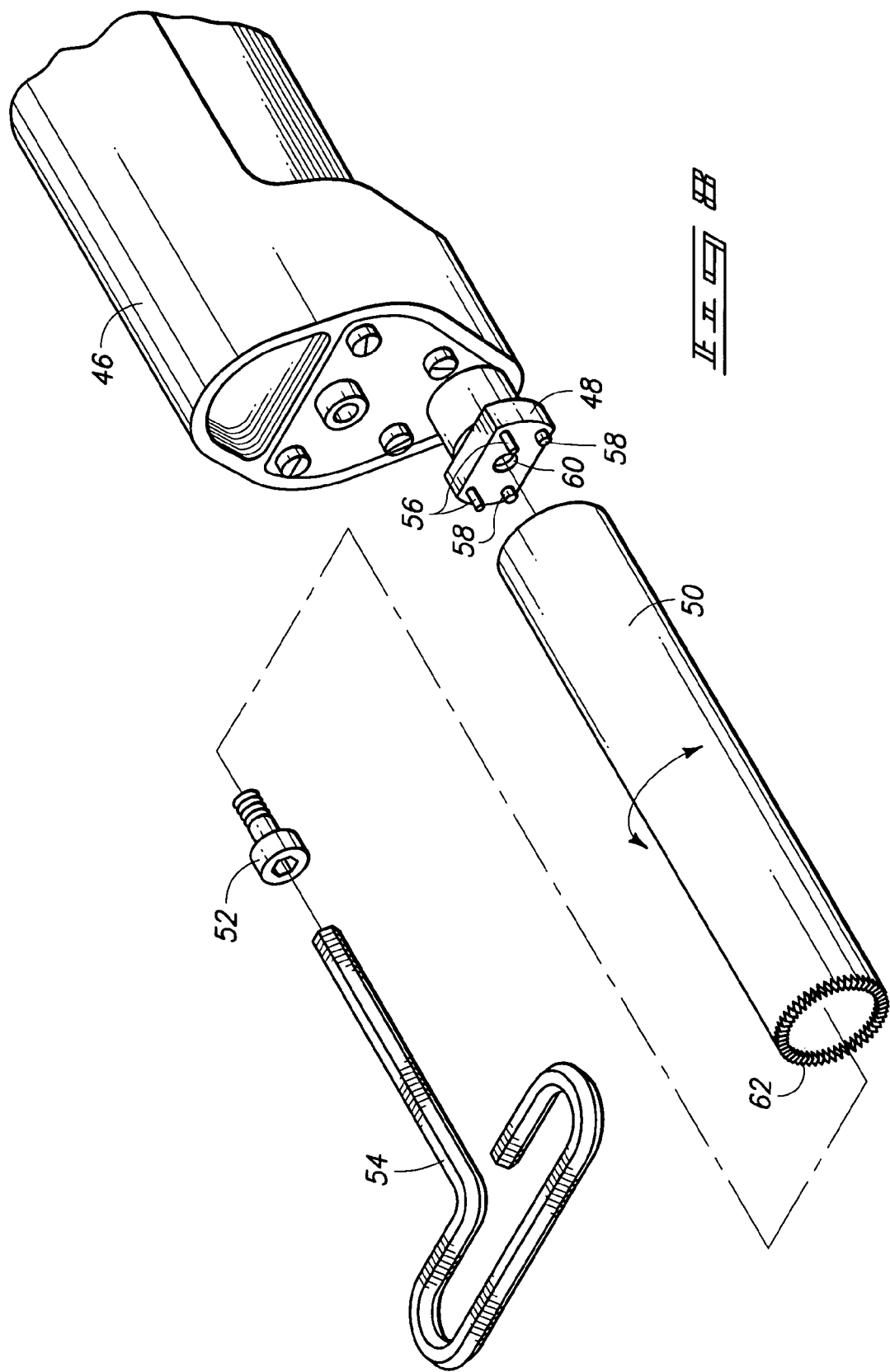
FIG. 8 is a perspective view of an alternative hole saw usable with a power tool for cutting a cylindrical kerf within the vertebral bodies of FIG. 7.
Figure 9:
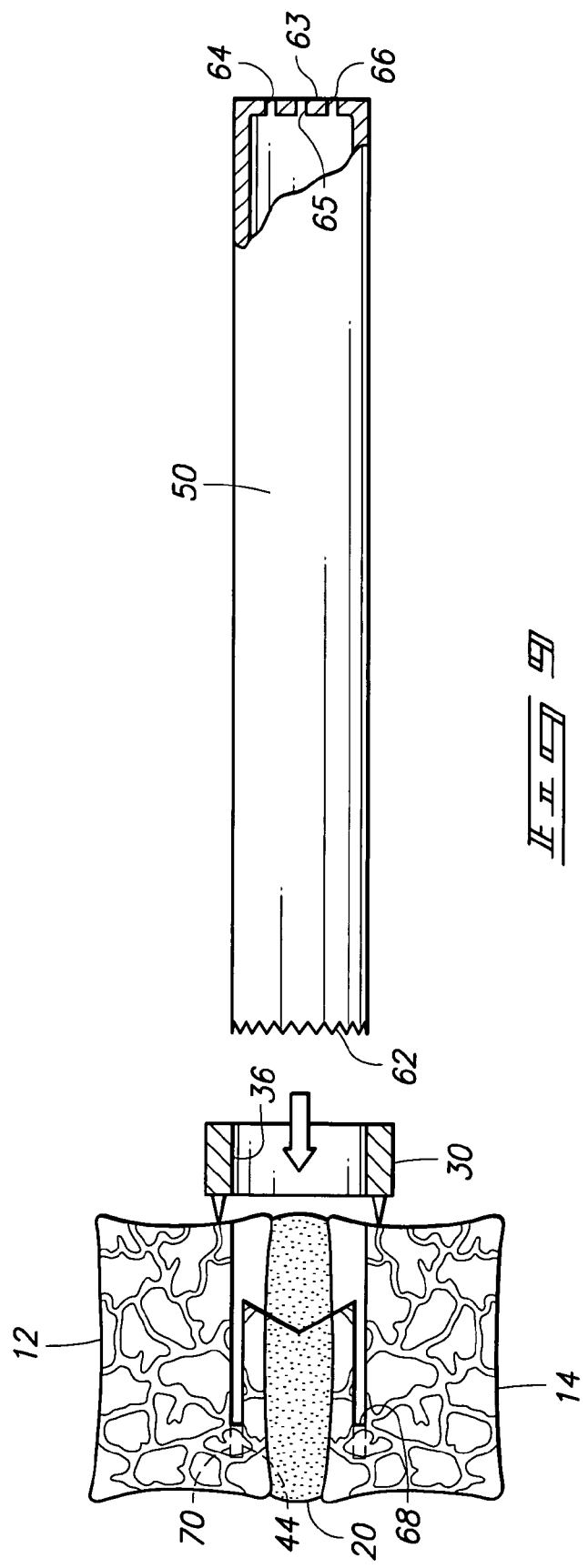
FIG. 9 is a simplified sagittal view illustrating the alternative hole saw usable with a power tool of FIG. 8 cutting a cylindrical kerf within the pair of vertebrae.

FIG. 8 illustrates one suitable construction for a reciprocating cylindrical blade 50 used in conjunction with hole saw 42 (of FIGS. 6 and 7) and tool 72 (of FIGS. 10 and 11) to form cylindrical kerf 44. More particularly, cylindrical blade 50 comprises a specially constructed reciprocating blade designed for use with an existing, or slightly modified, Stryker hand-held saw 46. Several Stryker hand-held saws are commercially available for producing reciprocating saw blade motion. Stryker Corporation is located in Kalamazoo, Mich., and develops, manufactures, and markets specialty surgical instruments.

As shown in FIGS. 8 and 9, cylindrical blade 50 comprises a hollow cylindrical metal tube with a leading end forming a plurality of cutting teeth 62, and a trailing end forming an end wall 63. End wall 63 of FIG. 9 contains a pair of small apertures 64 positioned above a pair of enlarged apertures 66. Apertures 64 and 66 are sized and positioned in end wall 63 so as to mount cylindrical blade 50 coaxially about the axis of rotation generated by saw blade drive member 48 on Stryker saw 46. Pins 56 and 58 interdigitate with apertures 64 and 66, respectively to impart rotatable securement between blade 50 and drive member 48. A threaded hexagonal fastener 52 is received through a bore 65 in end wall 63 and into a complementary threaded aperture 60 within drive member 48 so as to rigidly secure blade 50 onto drive member 48 for reciprocation.

In operation, drive member 48 is driven in reciprocating pivotal movement by saw 46, which imparts reciprocation to blade 50 and teeth 62 so as to generate cutting forces. Such cutting forces are directed against an object such as vertebral bodies 12 and 14 and disc 20 as shown in FIG. 9. Cylindrical blade 50 is sized with a dimension close to that of bore 36 of tool guide 30 such that saw blade 50 is axially guided in coaxial relation within bore 40 (see FIG. 7) and cylindrical groove 68 (see FIG. 9). Cylindrical blade 50 is used to cut all the way from groove 68 and to groove 70 which is substantially the entire depth of the finished kerf 44 (of FIG. 11).

Figure 10:
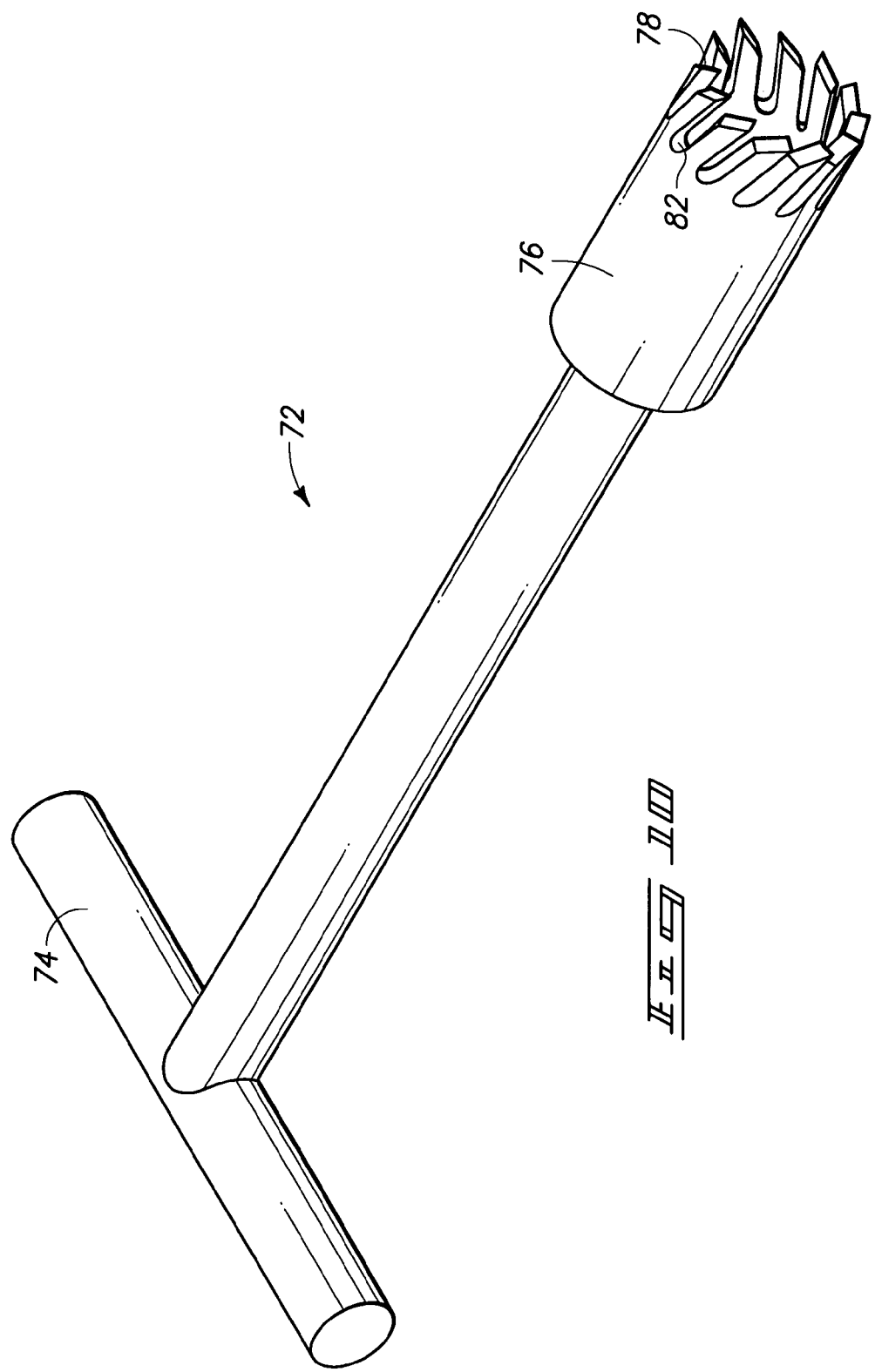
FIG. 10 is a perspective view of a kerf cleaning/deburring tool for cleaning debris from the cylindrical kerf formed within the vertebral bodies.
Figure 11:
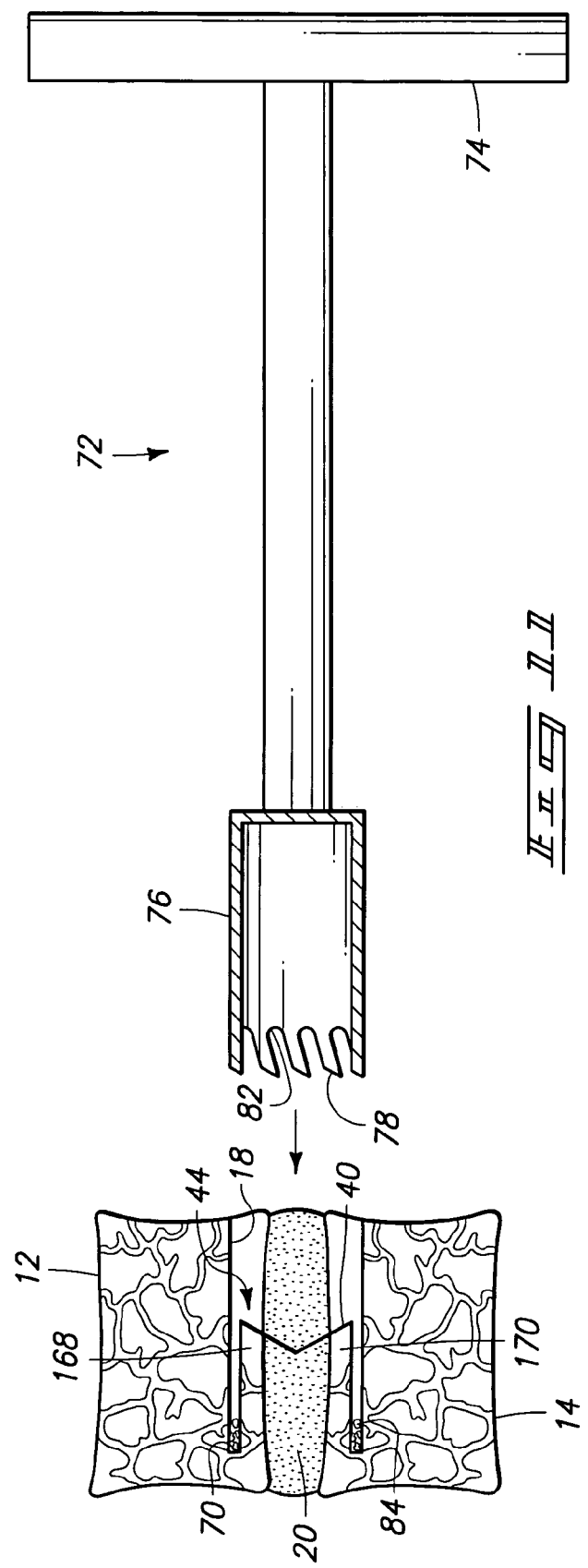
FIG. 11 is a simplified sagittal view showing the kerf cleaning/deburring tool of FIG. 10 and illustrating the removal of debris from within the cylindrical kerf formed within the vertebral bodies.

FIG. 10 illustrates one construction for a kerf cleaning/deburring tool 72 used to remove debris 84 from within cylindrical groove 70 of vertebral bodies 12 and 14 (see FIG. 11). Tool 10 includes a t-shaped handle 74 and a hollow cylindrical cutting body 76 having an open end terminating in a plurality of circumferentially spaced apart cutting teeth 78. A deep gullet, or throat, 82 is provided between adjacent teeth 78 for collecting debris that is removed when tool 10 is inserted and rotated within cylindrical groove 70 (see FIG. 11). Each gullet 82 has a pair of parallel sidewalls ending in a base that is opposite a throat. Each gullet 82 has a depth at least twice the width between the sidewalls. Furthermore, the gullets 82 are configured in one of a clockwise helical array and a counterclockwise helical array.

FIG. 11 shows tool 72 in partial breakaway view positioned to clean out debris 84 from cylindrical groove 70. Tool 72 is inserted into groove while handle 74 is rotated back and forth to impart back and forth rotary movement to teeth 78 within groove 70. Debris 84 is removed and cut from groove 70 by movement of teeth 78. Such debris 84 lodges in gullets and within the hollow interior of body 76. Tool 72 is then removed from groove 70 which also removes debris 84. Furthermore, teeth 78 impart a final finished dimension to cylindrical kerf 44 prior to inserting an implant therein.

Figure 12:
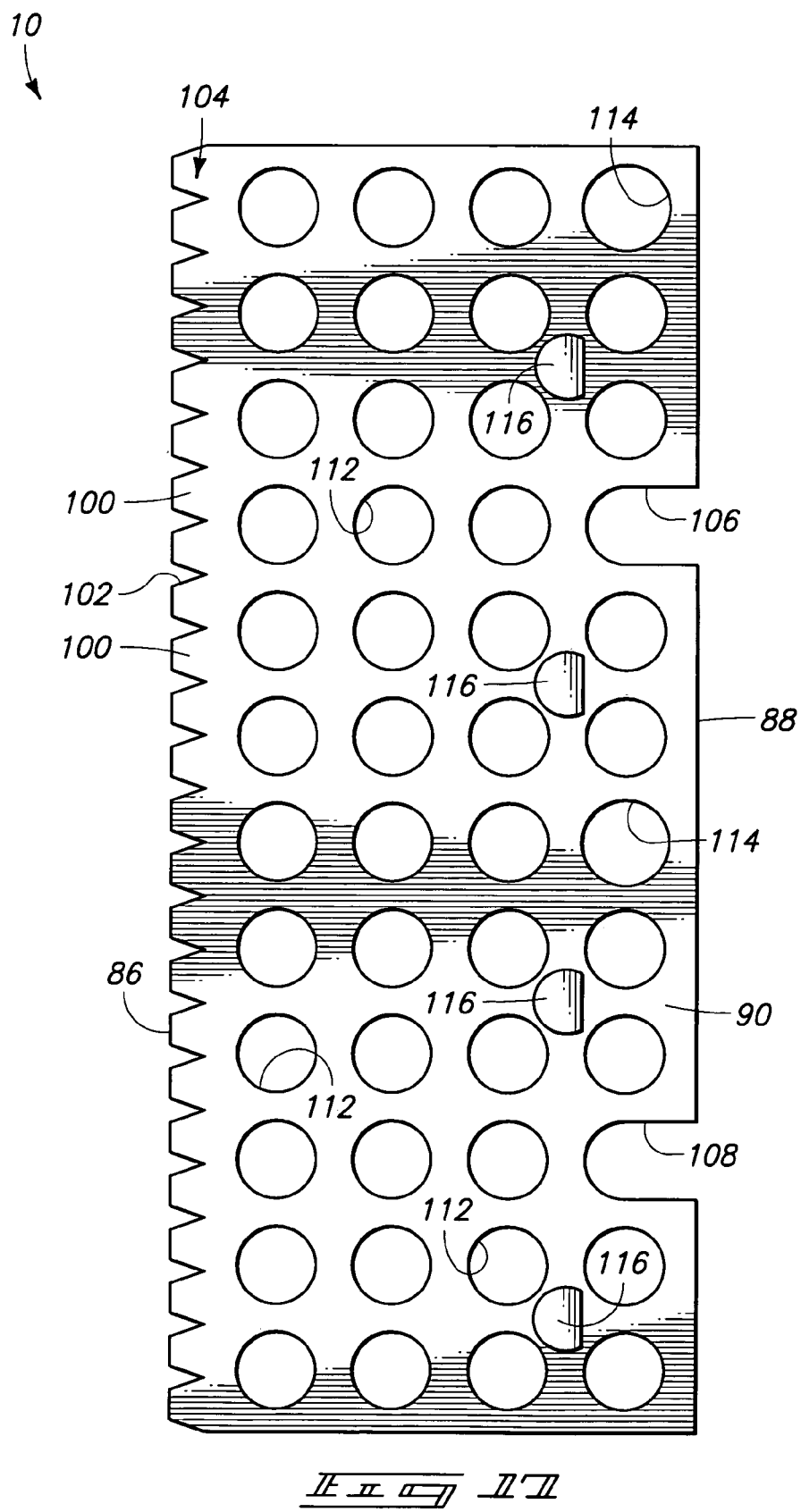
FIG. 12 is a perspective view of the vertebral interbody implant of FIG. 1 for insertion within the prepared bone beds of FIG. 11.

FIG. 12 illustrates self-distracting and fixating implant 10 in perspective view. Implant 10 has a cylindrical leading edge 86 and a trailing edge 88. An oblique outer surface 90 and a cylindrical inner surface 92 are formed between edges 86 and 88. A central cylindrical chamber, or aperture, 94 is formed within implant 10, between edges 86 and 88. Chamber 94 forms an open leading end 96 and an open trailing end 98 within implant 10. Upon implantation, open leading end 96 entraps projections 168 and 170 as shown in FIGS. 21 and 22 which imparts immediate fixation between vertebral bodies 12 and 14.

As shown in FIG. 12-17, four discrete beveled retaining tabs 116 are formed on oblique outer surface 90 adjacent to trailing end 88. Tabs 116 are positioned about surface 90 so as to engage within one of the bone beds formed in the vertebral bodies being joined. Such fingers have a ramped front face and a sharp rear edge that serves to facilitate insertion of implant 10 between prepared bone beds, while preventing dislodgement therefrom. More particularly the sharp rear edges of tabs 116 serve to engage with such bone beds, preventing inadvertent dislodgement of implant 10 from between a pair of prepared bone beds.

As shown in FIGS. 12-15 and 17, a plurality of interruptions 102 are formed in cylindrical leading edge 86, and extending into a tapered portion 104. Such interruptions comprise wedge-shaped removed portions of tapered portion 104 which cooperate to form individual tapered fingers 100 extending from cylindrical leading edge 86. Interruptions 102 serve to further collect any debris that still remains within cylindrical kerf 44 during insertion as shown in FIG. 22.

Also shown in FIGS. 12-15 and 17, a plurality of fenestrations 112 are provided spaced apart and extending through the tubular wall of implant 10. Such fenestrations 112 serve to facilitate bony ingrowth and through growth, and generally staged fusion as discussed in Applicant's issued U.S. Pat. No. 5,709,683 incorporated herein by reference. Additionally, a pair of slightly larger sized tool fenestrations 114 are provided along trailing edge 88 for receiving pins 144 and 146 of an insertion tool 120, as shown and described in greater detail below with reference to FIG. 18. Tool fenestrations 114 are positioned at locations perpendicular to guide slots 106 and 108; namely, at the 3 o'clock and 9 o'clock positions. During insertion, guide slots 106 and 108 are used to visual guide placement of implant 10 so as to impart self-distraction to adjacent vertebral bodies, as described in further detail below.

Such bony ingrowth and through-growth occur following insertion of implant 10 within bone beds defined by inner surfaces 160 and 164 and outer surfaces 162 and 166 as shown in FIG. 23. More particularly, remodeled bony ingrowth and through-growth are shown and described below in FIGS. 24 and 25. Fenestrations 112 extend substantially throughout the walls of tubular implant 10, particularly as shown in FIG. 17. Such fenestrations 112 offer avenues of ingrowth of bone between vertebrae, which is stimulated by bone graft material placed within a central chamber comprising cylindrical aperture 94 (see FIG. 15). In this manner, fenestrations 112 serve to facilitate earlier and more thorough ingrowth of bone within implant 10. Furthermore, fenestrations 112 enhance overall through growth of bone through implant 10.

A pair of guide slots 106 and 108 are also provided on a trailing end 88 of implant 10 to facilitate proper presentation and alignment when inserting implant 10 between a pair of vertebral bodies. Guide slots 106 and 108 are positioned at the 12 o'clock and 6 o'clock positions during insertion, corresponding with superior and inferior locations. Such positioning is crucial since implant 10 has an oblique outer surface that is designed to impart distraction between adjacent vertebra during insertion therebetween.

According to FIG. 17, oblique outer surface 90 of implant 10 is shown in an unrolled plan view to better depict layout of fenestrations 112, tool fenestrations 114, fingers 100, tabs 116 and guide slots 106 and 108. Tapered portion 104 is also shown extending along leading edge 86. Guide slots 106 and 108 are shown positioned along opposite trailing edge 88.

One feature of Applicant's invention is provided by forming a cylindrical leading edge 86, and an oblique outer surface 90. Edge 86 is inserted into an appropriately sized cylindrical kerf 44 (see FIG. 21), and insertion pressure is applied sufficient to generate distraction between adjacent vertebrae as leading tapered portion 104 is inserted therein. Hence, vertebrae 12 and 14 are distracted following implantation of implant 10 therebetween.

FIG. 18 illustrates an insertion tool or instrument 120 configured for loading implant 10 into prepared bone beds formed by kerf 44 and bore 40 (see FIG. 11). More particularly, bone beds are provided by a pair of inner surfaces 160, 164 and a pair of outer surfaces 162, 166 formed at least in part by kerf 44 as viewed in FIGS. 19 and 20.

Insertion tool 120 is formed from a driver 122 and a guide 124. Guide 124 forms a threaded bore 125 in which driver 122 is received in adjustable, threaded engagement via threaded portion 150 of driver 122. An adjustment nut 126 cooperates with a lock nut 128 to enable securement of driver 122 within guide 124 at a desired, threaded axial location.

Once driver 122 has been threaded sufficiently into guide 124 to cause pins 140 and 142 to be moved outwardly via contact with end 148, nut 126 is tightened into engagement against trailing end 138. Subsequently, lock nut 128 is tightened into engagement against nut 126.

A recessed mounting surface 130 is formed adjacent a leading end 137 of guide 124. Surface 130 is sized to slidably fit securely within open trailing end 98 (see FIGS. 13 and 16) of implant 10. Once positioned over surface 130 and against a receiving shelf 134, implant 10 is locked onto guide 124 by outwardly biasing a pair of retaining pins 140 and 142 within tool fenestrations 114. Preferably, pins 140 and 142 are sized sufficiently to fit within tool fenestrations 144, but are oversized relative to fenestrations 112 (of FIGS. 12-17). Hence, pins 140 and 142 are sized to prevent misaligned mounting of implant 10 onto insertion tool 120.

More particularly, driver 122 forms a driver pin 156 that extends within an enlarged bore 136 formed within guide 124. Bore 136 decreases in size immediately adjacent leading end 137 so as to form a reduced diameter bore 132. Bore 132 enables clearance of a beveled frustoconical end 148 of driver pin 156 during threaded adjustment between driver 122 and guide 124. Frustoconical end 148 mates in sliding engagement with a radially inwardly extending end of each pin 140 and 142. Such inward end of each pin 140 and 142 forms a complementary beveled end that mates for sliding engagement with end 148 as driver 122 is adjustably positioned within guide 124.

Pins 140 and 142 are retained for radially extending inward/outward movement within associated guide holes 144 and 146, respectively. More particularly, each pin 140 and 142 is retained within hole 144 and 146 via a press-fit rolled pin 141 and 143, respectively. Each rolled pin 141 and 143 passes through an elongated slot formed through each associated pin 141 and 143. In this manner, each pin 141 and 143 is allowed to slide within guide hole 144 and 146, respectively, but is prevented from becoming completely dislodged.

In order to facilitate insertion of implant 10, driver 122 has an enlarged driver handle 152 that terminates to form a driver end 154. Driver end 154 is shaped to facilitate impact with a hammer during insertion of an implant 10 between bone bodies. Furthermore, pins 140 and 142 cooperate with recessed mounting surface 130 and shelf 134 to rigidly and securely retain implant 10 on tool 120, even where considerable lateral loading might occur. Such lateral loading might occur, for example, as a result of wiggling implant 10 and tool 120 while attempting to insert implant 10 within a pair of prepared vertebrae. Upon insertion, implant 10 traps adjacent vertebrae for immediate fixation, within open leading end 96.

Once implant 10 has been inserted between bone bodies, nuts 126 and 128 are loosened, after which driver 122 is loosened or unthreaded relative to guide 124 which enables pins 140 and 142 to retract. Preferably, the outermost ends of pins 140 and 142 are chamfered to facilitate removal of implant 10 from tool 120. Optionally, frustoconical end 148 can be magnetized to impart retraction of pins 140 and 142 as drive pin 156 is retracted within guide 124.

FIGS. 19 and 20 illustrate prepared vertebrae 12 and 14 prior to insertion of an implant and after insertion of an implant of Applicant's invention, respectively, but with the implant omitted for clarity. FIG. 21 corresponds with FIG. 20, but shows the details of implant 10 inserted in interlocking relation with vertebrae 12 and 14.

As shown in FIG. 19, a pair of vertebrae 12 and 14 are retained together with an intervertebral disc 20. An aperture 18 is formed partially as a kerf 44, and generates bone beds in the form of inner surfaces 160, 164 and outer surfaces 162, 166. A pair of intact bone projections 168 and 170 are formed as a result extending from vertebrae 12 and 14, respectively. Such bone projections 168 and 170 are entrapped within the open leading end 96 of implant 10 (see FIG. 12) immediately upon insertion. Hence, instant fixation is provided upon implant of such device. Furthermore, instant distraction is also generated as a result of the oblique outer surface 90 of implant 10 (see FIG. 12).

As shown in FIG. 20, the forcible insertion of an implant between bone bodies, or vertebrae, 12 and 14 causes self-distraction of amount "D" which corresponds to the difference in diameter for cylindrical leading edge 86 and the outermost dimension of oblique surface 90 along the vertical direction, as shown in FIG. 15. Dimension "D" is shown slightly exaggerated in FIG. 20 to more clearly illustrate the self-distraction feature. In most applications, a lumbar placement would generate approximately 5 millimeters of distraction distance "D".

FIG. 21 illustrates implant 10 inserted into vertebrae 12 and 14. Due to the difference in wall thickness caused by the oblique outer surface and cylindrical inner surface of implant 10, cylindrical kerf 44 only receives implant 10 snugly at the 12 o'clock (superior) and 6 o'clock (inferior) positions as shown in FIG. 21. Tabs 116 are also shown inserted into vertebrae 12 and 14 which ensures retention of implant 10 therein, following implantation. Furthermore, the oblique outer surface mates in conforming engagement with the prepared bone beds in vertebrae 12 and 14 such that lateral bending and rotation is resisted due to the increased frictional forces caused by close fit-up, and due to non-cylindrical mating contact.

As shown in FIG. 21, implant 10 generates self-distraction between vertebrae 12 and 14, once implanted. The annulus is thereby placed on stretch which further stabilizes instant fixation. The non-cylindrical fit-up between implant 10 and vertebrae 12 and 14 cooperates with the stretched annulus so as to impart rigid, instant fixation. Furthermore, implant 10 stops further compression from occurring between vertebrae 12 and 14. Likewise, implant 10 entraps bone projections 168 and 170, which prevents any further distraction from occurring between vertebrae 12 and 14.

FIG. 22 shows implant 10 during implantation between vertebrae 12 and 14, in a self-distracted position. Bone projections 168 and 170 are clearly shown entrapped within implant 10, which generates immediate entrapment of projections 168 and 170, and fixation between vertebrae 12 and 14. After removal and retraction of tool 124, bone grafts, or morsels, 171 are then packed inside of implant 10, as shown in FIG. 23.

According to FIG. 23, bone grafts 171 facilitate earlier bone ingrowth and through growth. Similarly, fenestrations, as well as the open leading and trailing ends, of implant 10 further facilitate such ingrowth and through growth.

FIG. 24 illustrates staged stabilization and fusion via Wolff's law, wherein bone remodeling and reorganization has further fixed and fused such adjacent vertebrae 12 and 14. The trabeculae relocate through fenestrations to form a mature strengthening of the trabeculae. Additional reorganization is provided by preparing bone beds that recess implant 10 within vertebrae, and by providing bone graft material thereabout at the time of implantation. Accordingly, additional bone reorganization is facilitated outside of implant 10.

FIG. 24 is a sagittal section and diagrammatic view through implant 10 and vertebrae 12 and 14, illustrating reorganization of fused bone material through implant 10. Histologic bone cell geometry is shown in greater detail, corresponding in time with complete bone remodeling. Lacunae and canals or voids 172 are formed between the trabeculae of bone 174.

FIG. 25 is a coronal and diagrammatic view taken perpendicular to the view of FIG. 24 along line 25-25. In such view, bone cells have remodeled to form a definite elongated configuration extending between vertebrae 12 and 14. Such remodeled bone through growth can be seen between fenestrations on some sides of a patient, occurring from cephalad to caudad, as well as between fenestrations along a diagonal configuration of the patient, from cephalad to caudad.

Figure 26:
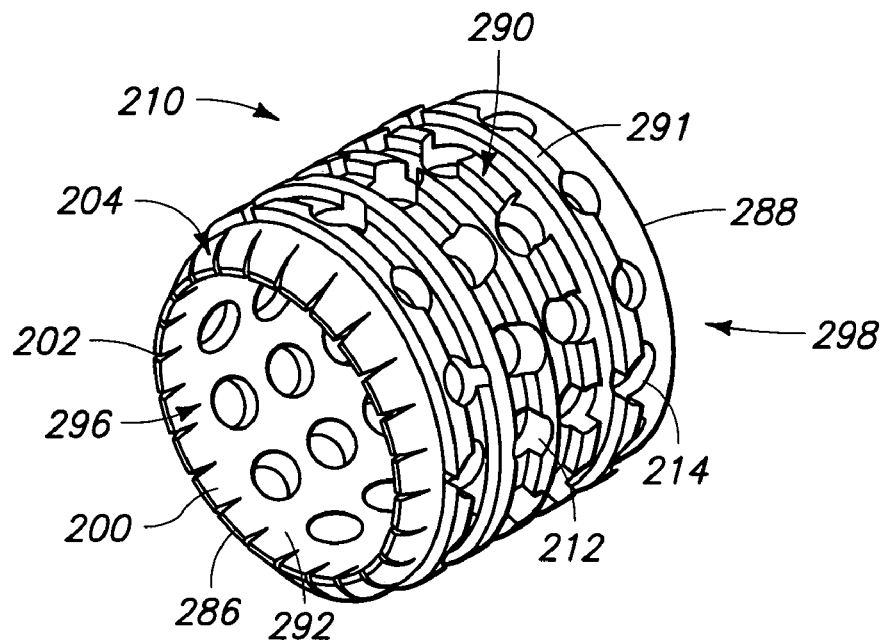
FIG. 26 is a perspective view of an alternatively constructed vertebral interbody implant similar to the embodiment depicted in FIGS. 1-25 for insertion within the prepared bone beds of FIG. 11.
Figure 27:
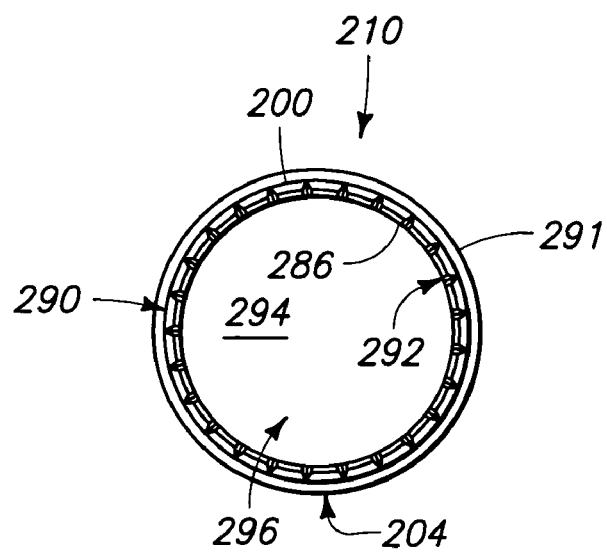
FIG. 27 is a frontal view of the vertebral interbody implant of FIG. 26.

FIGS. 26 and 27 illustrate an alternative embodiment self-distracting and fixating implant 210. FIG. 26 illustrates implant 210 in perspective view. Implant 210 is constructed similarly to implant 10 depicted in FIG. 12. However, implant 210 is provided with a cylindrical outer surface 290 containing at least one helical thread 291. Implant 210 has a cylindrical leading edge 286 and a cylindrical trailing edge 288. Cylindrical outer surface 290 and a cylindrical inner surface 292 are formed between edges 286 and 288. A central cylindrical chamber, or aperture, 294 (see FIG. 27) is formed within implant 210, between edges 286 and 288. Chamber 294 forms an open leading end 296 and an open trailing end 298 within implant 210. Upon implantation, open leading end 296 entraps bone projections similar to those shown in FIGS. 21 and 22 on implant 10. Accordingly, instant fixation is provided between vertebral bodies.

Also shown in FIGS. 26 and 27, a plurality of interruptions 202 are formed in cylindrical leading edge 286, and extending into a tapered portion 204. Individual tapered fingers 200 are formed by interruptions 202, along cylindrical leading edge 286. Interruptions 202 serve to collect debris similar to the interruptions depicted for implant 10 of FIG. 12.

Although implant 210 does not include an oblique outer surface, a tapered portion 104 extends along leading edge 286 so as to impart a degree of distraction when inserted into the cylindrical kerf 44, shown in FIG. 20. However, the cylindrical threaded outer surface 290 will not generate quite the same degree of distraction, and will not impart the same degree of fit-up as will implant 10 of FIG. 21.

Implant 210 also includes tool fenestrations 214 for facilitating insertion with tool or instrument 120 of FIG. 18. Furthermore, implant 210 includes a plurality of fenestrations 212 for facilitating bony ingrowth and through growth following insertion of implant 210 within bone bodies of adjacent vertebral bodies.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

The invention claimed is:

1. An apparatus for preparing a spinal implant surgical site for receiving a spinal fusion implant, comprising:
    a drive shaft;
    a handle carried by the drive shaft; and
    a hollow, cylindrical cutting body provided at a leading end of the drive shaft having an open leading end, a plurality of circumferentially spaced-apart cutting teeth provided on the open leading end, and a plurality of circumferentially spaced-apart gullets each provided between an adjacent pair of the cutting teeth, each of the gullets having a pair of parallel sidewalls ending in a base that is opposite a throat, and each of the gullets having a depth at least twice the width between the sidewalls.

2. The apparatus of claim 1, wherein the drive shaft comprises an elongate, cylindrical drive shaft.

3. The apparatus of claim 2, wherein the handle comprises a t-shaped handle integrally formed onto a trailing end of the cylindrical drive shaft.

4. The apparatus of claim 1, wherein the hollow, cylindrical cutting body has a cylindrical outer wall and a concentric cylindrical inner wall, wherein the cylindrical inner wall extends from the open leading end into the body from a leading end toward a trailing end.

5. The apparatus of claim 4, wherein the cylindrical inner wall is sized with a uniform dimension cross-section extending from the leading end toward the trailing end.

6. The apparatus of claim 1, wherein the handle comprises a tactile gripping surface configured to facilitate tactile manipulation of the apparatus.

7. The apparatus of claim 1, wherein the hollow, cylindrical body has a closed trailing end comprising a cylindrical end wall affixed onto a leading end of the drive shaft.

8. The apparatus of claim 1, wherein the cutting teeth are all configured in one of a clockwise cutting array and a counterclockwise cutting array.

9. A kerf cleaning tool for bone bodies, comprising:
    a handle support member;
    a handle carried by the handle support member; and
    a cutting head provided at a leading end of the handle support member having an open leading end, a cylindrical bore extending from the open leading end, a plurality of circumferentially spaced-apart cutting teeth provided along the open leading end, and a plurality of circumferentially spaced-apart gullets each provided between an adjacent pair of the cutting teeth, each of the gullets having a pair of parallel sidewalls ending in a base that is opposite a throat, each of the gullets having a depth at least twice the width between the sidewalls, and each of the gullets configured in one of a clockwise helical array and a counterclockwise helical array.

10. The kerf cleaning tool of claim 9, wherein the handle comprises a t-shaped handle integrally formed from the handle support member.

11. The kerf cleaning tool of claim 9, wherein the cutting head comprises a cylindrical cutting body.

12. The kerf cleaning tool of claim 9, wherein the cutting head comprises a cylindrical outer surface and a concentric, cylindrical inner surface defining, at least in part, the cylindrical bore.

13. The kerf cleaning tool of claim 9, wherein the cutting head, the handle support member, and the handle are integrally formed together.

14. The kerf cleaning tool of claim 9, wherein the cutting head has a cylindrical wall portion defining, at least in part, the cylindrical bore, and wherein the cutting teeth are integrally formed along the leading end of the cylindrical wall portion.

15. A method of shaping a kerf within at least one bone body, comprising:
    providing a kerf shaping tool having a cylindrical cutting body along a leading end of a drive shaft, the body having an open leading end, a cylindrical bore extending from the open leading end, a plurality of circumferentially spaced-apart cutting teeth provided on the open leading end, and a plurality of circumferentially spaced-apart gullets each provided between an adjacent pair of the cutting teeth;

inserting the cylindrical cutting body into a cylindrical kerf provided by at least one bone body;

rotating the tool within the kerf to cut bone chips from the at least one bone body; and depositing the chips in one or more of the gullets for removal from the kerf with the tool.

16. The method of claim 15, wherein rotating comprises oscillating the tool within the kerf.

17. The method of claim 15, further comprising withdrawing the tool and the chips from within the kerf after depositing the chips in the one or more of the gullets.

18. The method of claim 15, wherein the cutting teeth are biased in one of a clockwise direction and a counter-clockwise direction.

19. The method of claim 18, wherein rotating comprises rotating the tool in the one of the clockwise direction and the counter-clockwise direction.

20. The method of claim 15, wherein inserting and rotating are performed concurrently.

21. An apparatus for preparing a spinal implant surgical site for receiving a spinal fusion implant, comprising:
an elongate, cylindrical drive shaft;
a t-shaped handle integrally formed onto a trailing end of the cylindrical drive shaft; and
a hollow, cylindrical cutting body provided at a leading end of the drive shaft having an open leading end, a plurality of circumferentially spaced-apart cutting teeth provided on the open leading end, and a plurality of circumferentially spaced-apart gullets each provided between an adjacent pair of the cutting teeth, each of the gullets having a pair of parallel sidewalls ending in a base that is opposite a throat, and each of the gullets configured in one of a clockwise helical array and a counterclockwise helical array.

22. An apparatus for preparing a spinal implant surgical site for receiving a spinal fusion implant, comprising:
a drive shaft;
a handle carried by the drive shaft; and
a hollow, cylindrical cutting body having a cylindrical outer wall and a concentric cylindrical inner wall, the cylindrical inner wall extending from the open leading end into the body from a leading end toward a trailing end, the cutting body provided at a leading end of the drive shaft having an open leading end, a plurality of circumferentially spaced-apart cutting teeth provided on the open leading end, and a plurality of circumferentially spaced-apart gullets each provided between an adjacent pair of the cutting teeth, each of the gullets having a pair of parallel sidewalls ending in a base that is opposite a throat, and each of the gullets having a depth at least twice the width between the sidewalls.

23. The apparatus of claim 22, wherein the cylindrical inner wall is sized with a uniform dimension cross-section extending from the leading end toward the trailing end.

24. An apparatus for preparing a spinal implant surgical site for receiving a spinal fusion implant, comprising:
a drive shaft;
a handle carried by the drive shaft; and
a hollow, cylindrical cutting body provided at a leading end of the drive shaft having an open leading end, a plurality of circumferentially spaced-apart cutting teeth provided on the open leading end, and a plurality of circumferentially spaced-apart gullets each provided between an adjacent pair of the cutting teeth, wherein the cutting teeth are all configured in one of a clockwise cutting array and a counterclockwise cutting array, each of the gullets having a pair of parallel sidewalls ending in a base that is opposite a throat, and each of the gullets having a depth at least twice the width between the sidewalls.

* * * * *

UNITED STATES PATENT AND TRADEMARK OFFICE
CERTIFICATE OF CORRECTION

| | |
|---|---|
| PATENT NO. | : 7,553,313 B2 |
| APPLICATION NO. | : 11/224412 |
| DATED | : June 30, 2009 |
| INVENTOR(S) | : Bagby |

It is certified that error appears in the above-identified patent and that said Letters Patent is hereby corrected as shown below:

Column 10, Line 21 – Replace "Thereafter." with --Thereafter--.

Column 10, Line 28-29 – Replace "pre-pared" with --pre-pare--.

Signed and Sealed this

Seventh Day of September, 2010

David J. Kappos
*Director of the United States Patent and Trademark Office*